(12) United States Patent
Breitenbucher et al.

(10) Patent No.: US 8,598,356 B2
(45) Date of Patent: Dec. 3, 2013

(54) HETEROARYL-SUBSTITUTED UREA MODULATORS OF FATTY ACID AMIDE HYDROLASE

(75) Inventors: J. Guy Breitenbucher, Escondido, CA (US); John M. Keith, San Diego, CA (US); Mark S. Tichenor, San Diego, CA (US); Alison L. Chambers, San Diego, CA (US); William M. Jones, San Diego, CA (US); Natalie A. Hawryluk, San Diego, CA (US); Amy K. Timmons, Renton, WA (US); Jeffrey E. Merit, Stanford, CA (US); Mark J. Seierstad, Escondido, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/131,061

(22) PCT Filed: Nov. 24, 2009

(86) PCT No.: PCT/US2009/065752
§ 371 (c)(1),
(2), (4) Date: May 25, 2011

(87) PCT Pub. No.: WO2010/068452
PCT Pub. Date: Jun. 17, 2010

(65) Prior Publication Data
US 2011/0230490 A1 Sep. 22, 2011

Related U.S. Application Data

(60) Provisional application No. 61/117,880, filed on Nov. 25, 2008.

(51) Int. Cl.
*C07D 211/68* (2006.01)
*A61K 31/445* (2006.01)
(52) U.S. Cl.
USPC .......................................... 546/194; 514/318
(58) Field of Classification Search
USPC .......................................... 546/194; 514/318
See application file for complete search history.

(56) References Cited

U.S. PATENT DOCUMENTS

| | | | |
|---|---|---|---|
| 6,100,279 A | 8/2000 | Vaccaro et al. | |
| 6,124,299 A | 9/2000 | Baindur et al. | |
| 6,387,900 B1 | 5/2002 | Pevarello et al. | |
| 6,395,740 B1 | 5/2002 | Baindur et al. | |
| 6,881,741 B2 | 4/2005 | Chan Chun Kong et al. | |
| 2003/0047569 A1 | 3/2003 | Chirnomas | |
| 2003/0149036 A1 | 8/2003 | Flohr et al. | |
| 2006/0173184 A1 | 8/2006 | Apodaca et al. | |
| 2007/0004741 A1 | 1/2007 | Apodaca et al. | |
| 2007/0270433 A1 | 11/2007 | Brinkman et al. | |

FOREIGN PATENT DOCUMENTS

| | | |
|---|---|---|
| WO | WO 02 087569 A1 | 11/2002 |
| WO | WO 03 047569 A1 | 6/2003 |
| WO | WO 2004 018428 A1 | 3/2004 |
| WO | WO 2004 033652 A2 | 4/2004 |
| WO | WO 2006 014136 A1 | 2/2006 |
| WO | WO 2006 074025 A1 | 7/2006 |
| WO | WO 2006 085108 A1 | 8/2006 |
| WO | WO 2007 096251 A1 | 8/2007 |
| WO | WO 2007 134958 A1 | 11/2007 |
| WO | WO 2008 023720 A1 | 2/2008 |
| WO | WO 2008 024139 A2 | 2/2008 |
| WO | WO 2008 047229 A2 | 4/2008 |
| WO | WO 2008 153752 A2 | 12/2008 |

OTHER PUBLICATIONS

U.S. Appl. No. 60/931,920, filed May 25, 2007, Breitenbucher et al.
U.S. Appl. No. 61/117,884, filed Nov. 25, 2008, Natalie Hawryluk.
Bagshawe et al "Antibody-Directed Enzyme Prodrug Therapy: A Review" Drug Development Research 1995 vol. 34 pp. 220-230.
Baker et al :Endocannabinoids Control Spasticity in a Multiple Sclerosis Model FASEB J 2001 vol. 15(2) pp. 300-302.
Baker et al "Cannabinoids Control Spasticity and Tremor in a Multiple Sclerosis Model" Nature 2000 vol. 404 pp. 84-87.
Berge et al "Pharmaceutical Salts" J Pharm Sci 1977 vol. 66 pp. 1-19.
Bertolini et al "A New Rational Hypothesis for the Pharmacophore of the Active Metabolite of Leflunomide, a Potent Immunosuppressive Drug" J Med Chem 1997 vol. 40 pp. 2011-2016.
Bodor et al "Novel Approaches to the Design of Safer Drugs: Soft Drugs and Site-Specific Chemical Delivery Systems",Adv Drug Res 1984 vol. 13 pp. 255-331.
Boger et al "Exceptionally Potent Inhibitors of Fatty Acid Amide Hydrolase: The Enzyme Responsible for Degradation of Endogenous Oleamide and Ananmide" Proc Natl Acad Sci USA 2000 vol. 97(1) pp. 5044-5049.
Bouaboula et al "Anandamine Induced PPARγ Transcriptional Activation and 3T3-L1 Preadipocyte Differentiation" Eur J Pharmacol 2005 vol. 517 pp. 174-181.
Bundgaard et al Design of Prodrugs Ed H. Bundgaard Elsevier 1985.
Croxford et al "Cannabinoid-Mediated Neuroprotectin, Not Immunosuppression, May Be More Relevant to Multiple Sclerosis" J Neuroimmunol 2008 vol. 193 pp. 120-129.
Cravatt et al "Novel Mechanistic Class of Fatty Acid Amide Hydrolase Inhibitors With Remarkable Selectivity" Biochemistry 2007 vol. 46(45) pp. 13019-13030.
Cravatt et al "Chemical Characterization of a Family of Brain Lipids That Induce Sleep" Science 1995 vol. 268 pp. 1506-1509.
Cravatt et al "Molecular Characterization of an Enzyme That Degrades Neuromodulatory Fatty-Acid Amides" Nature 1996 vol. 384 pp. 83-87.

(Continued)

*Primary Examiner* — John Mabry

(57) ABSTRACT

Certain heteroaryl-substituted piperidinyl and piperazinyl urea compounds are described, which are useful as FAAH inhibitors. Such compounds may be used in pharmaceutical compositions and methods for the treatment of disease states, disorders, and conditions mediated by fatty acid amide hydrolase (FAAH) activity, such as anxiety, pain, inflammation, sleep disorders, eating disorders, insulin resistance, diabetes, osteoporosis, and movement disorders (e.g., multiple sclerosis).

17 Claims, No Drawings

(56) References Cited

OTHER PUBLICATIONS

Cravatt et al "Supersensitivity to Anandamide and Enhanced Endogenous Cannabinois Signaling in Mice Lacking Fatty Acid Amide Hydrolase" Proc Natl Acad Sci USA 2001 vol. 98(16) pp. 9371-9376.

Devane et al "Isolation and Structure of a Brain Constituent That Binds to the Cannabinoid Receptor" Science 1992 vol. 258 pp. 1946-1949.

Fleisher et al "Improved Oral Drug Delivery: Solubility Limitations Overcome by the Use of Prodrugs" Adv Drug Delivery Rev 1996 vol. 19 pp. 115-140.

Gobbi et al "Antidepressant-Like Activity and Modulation of Brain Monoaminergic Transmission by Blockade of Anandamide Hydrolysis" Proc Natl Acad Sci USA 2005 vol. 102(51) pp. 18620-18625.

Goya et al "Recent Advances in Cannabioid Receptor Agonists and Antagonists" Exp Opin Ther Patents 2000 vol. 10 pp. 1529-1538.

Holt et al "Inhibitors of Fatty Acid Amide Hydrolase Reduce Carrageenan-Induced Hind Paw Inflammation in Pentobarbital-Treated Mice: Comparison With Indomethacin and Possible Involvement of Cannabinoid Receptors" Br J Pharmacol 2005 vol. 146 pp. 467-476.

Karsak et al "Cannabinoid Receptor Type 2 Gene is Associated With Human Osteoporosis" Hum Mol Genet 2005 vol. 14 pp. 3389-3396.

Kathuria et al "Modulation of Anxiety Through Blockade of Anandamide Hydrolysis" Nat Med 2003 vol. 9(1) pp. 76-81.

Kirkham et al "Endocannabinoid Levels in Rat Limbic Forebrain and Hypothalamus in Relation to Fasting, Feeding and Satiation: Stimulation of Eating by 2-Arachidonoyl Glycerol" Br J Pharmacol 2002 vol. 136 pp. 550-557.

Lambert et al "The Palmitoylethanolamide Family: A New Class of Anti-Inflammatory Agents?" Curr Med Chem 2002 vol. 9(6) pp. 663-674.

Larsen et al Design and Applications of Prodrugs, Drug Design and Development Krogsgaard-Larsen et al., Eds Harwood Academic Publishers 1991.

Mendelson et al "The Hypnotic Actions of the Fattyacid Amide, Oleamide" Neuropsychopharmacology 2001 vol. 25 pp. S36-S39.

Ofek et al "Peripheral Cannabinoid Receptor, CB2, Regulates Bone Mass" Proc Natl Acad Sci USA 2006 vol. 103 pp. 696-701.

Overton et al "GPR119, A Novel G Protein-Coupled Receptor Target for the Treatment of Type 2 Diabetes and Obesity" Br J. Pharmacol 2008 vol. 153 pp. S76-S81.

Piomelli Daniele "The Molecular Logic of Endocannabinoid Signalling" Nat Rev Neuros 2003 vol. 4 (11) pp. 873-884.

Plutzky et al "Preventing Type 2 Diabetes and Cardiovascular Disease in Metabolic Syndrome: The Role of PPARα" Diab Vasc Dis Res 2007 4 Suppl 3 S12-14.

Robinson et al "Discovery of the Hemifumarate and (α-L-Alanyloxy)Methyl Ether As Prodrugs of an Antirheumatic Oxindole: Prodrugs for the Enolic OH Group" J Med Chem 1996 vol. 39 pp. 10-18.

Robson et al "Therapeutic Aspects of Cannabis and Cannabinoids" Br J Psychiatry 2001 vol. 178 pp. 107-115.

Rodriguez De Fonesca et al "An Anorexic Lipid Mediator Regulated by Feeding" Nature 2001 vol. 414 pp. 209-212.

Shan et al "Prodrug Strategies Based on Intramolecular Cyclization Reactions" J Pharm Sci 1997 vol. 86(7) pp. 765-767.

Stahl and Wermuth Eds Handbook of Pharmaceutical Salts, Properties, Selection and Use Stahl and Wermuth Eds Wiley-VCH and VHCA Zurich 2002.

Steffens et al "Low Dose Oral Cannabinoid Therapy Reduces Progression of Atherosclerosis in Mice" Nature 2005 vol. 434 pp. 782-786.

Svendsen et al "Does the Cannabinoid Dronabinol Reduce Central Pain in Multiple Sclerosis? Randomized Double Blind Placebo Controlled Crossover Trial" Br Med J 2004 vol. 329 pp. 253-260.

Ueda et al "Purification and Characterization of an Acid Amidase Selective for N-Palmitoylethanolamine, a Putative Endogenous Anti-Inflammatory Substance" J Biol Chem 2001 pp. 276(38) pp. 35552-35557.

Varvel et al "Fatty Acid Amide Hydrolase (-/-) Mice Exhibit an Increased Sensitivity to the Disruptive Effects of Anandamide or Oleamide in a Working Memory Water Maze Task" J Pharmacol Exp Ther 2006 vol. 317(1) pp. 251-257.

Webb et al "Genetic Deletion of Fatty Acid Amide Hydrolase Results in Improved Long Term Outcome in Chronic Autoimmune Encephalitis" Neurosci Lett 2008 vol. 439 pp. 106-110.

HETEROARYL-SUBSTITUTED UREA MODULATORS OF FATTY ACID AMIDE HYDROLASE

CROSS-REFERENCE TO RELATED APPLICATIONS

This application is a national phase of International Application No. PCT/US2009/065752 filed Nov. 24, 2009 and claims benefit of priority under 35 U.S.C. §119(e) of U.S. Provisional Application No. 61/117,880 filed Nov. 25, 2008.

FIELD OF THE INVENTION

The present invention relates to certain heteroaryl-substituted piperidinyl and piperazinyl urea compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

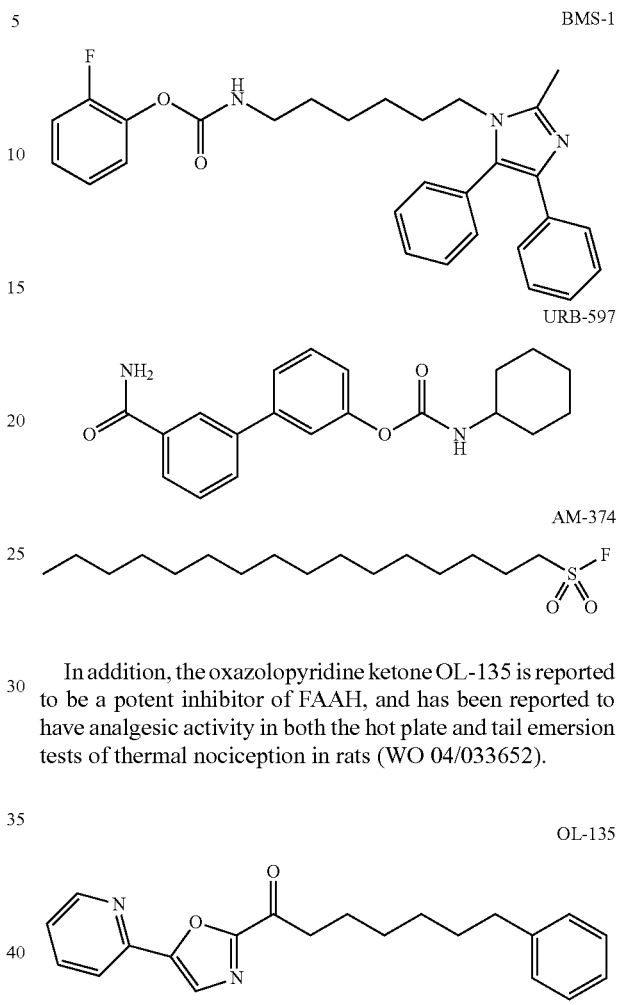

In addition, the oxazolopyridine ketone OL-135 is reported to be a potent inhibitor of FAAH, and has been reported to have analgesic activity in both the hot plate and tail emersion tests of thermal nociception in rats (WO 04/033652).

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reportedly initiated in Germany in May 2002.

A number of individuals with locomotor activity-related diseases, such as multiple sclerosis have claimed a benefit from cannabis for both disease-related pain and spasticity, with support from small controlled trials (Croxford et al., *J. Neuroimmunol*, 2008, 193, 120-9; Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD). It has been reported that FAAH knockout mice consistently recover to a better clinical score than wild type controls, and this improvement is not a result of anti-inflammatory activity, but rather may reflect some neuroprotection or remyelination promoting effect of lack of the enzyme (Webb et al, *Neurosci Lett.*, 2008, vol. 439, 106-110).

Reports of small-scale controlled trials to investigate other potential commercial uses of cannabinoids have been made. Trials in volunteers have been reported to have confirmed that oral, injected, and smoked cannabinoids produced dose-related reductions in intraocular pressure (1OP) and therefore may relieve glaucoma symptoms. Ophthalmologists have prescribed cannabis for patients with glaucoma in whom other drugs have failed to adequately control intraocular pressure (Robson, 2001, supra).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH −/− mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003, supra).

In addition to the effects of a FAAH inhibitor on AEA and other endocannabinoids, inhibitors of FAAH's catabolism of other lipid mediators may be used in treating certain other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel et al., *J. Pharmacol. Exp. Ther.* 2006, 317(1), 251-257) and depression (Gobbi et al., *Proc. Natl. Acad. Sci. USA* 2005, 102(51), 18620-18625).

Two additional indications for FAAH are supported by recent data indicating that FAAH substrate activated receptors are important in energy metabolism, and in bone homeostasis (Overton et al., *Br. J. Pharmacol.* 2008, in press; and Plutzky, *Diab. Vasc. Dis. Res.* 2007, 4 Suppl 3, S12-4). It has been shown that the previously mentioned lipid signaling fatty acid amides catabolized by FAAH, oleoylethanolamide (OEA), is one of the most active agonists of the recently de-orphanised GPCR 119 (GPR119) (also termed glucose dependent insulinotropic receptor). This receptor is expressed predominantly in the pancreas in humans and activation improves glucose homeostasis via glucose-dependent insulin release in pancreatic beta-cells. GPR119 agonists can suppress glucose excursions when administered during oral glucose tolerance tests, and OEA has also been shown independently to regulate food intake and body weight gain when administered to rodents, indicating a probable benefit in energy metabolism disorders, such as insulin resistance and diabetes. The FAAH substrate palmitoylethanolamide (PEA) is an agonist at the $PPAR\alpha$ receptor. Evidence from surrogate markers in human studies with the $PPAR\alpha$ agonist fenofibrate is supportive of the concept that $PPAR\alpha$ agonism offers the potential for inducing a coordinated $PPAR\alpha$ response that may improve dyslipidaemia, repress inflammation and limit atherosclerosis in patients with the metabolic syndrome or type 2 diabetes. The FAAH substrate anandamide (AEA) is an agonist at the $PPAR\gamma$ receptor. Anandamide treatment induces 3T3-L1 differentiation into adipocytes, as well as triglyceride droplet accumulation and expression of adiponectin (Bouaboula et al., *E. J. Pharmacol.* 2005, 517, 174-181). Low dose cannabinoid therapy has been shown to reduce atherosclerosis in mice, further suggesting a therapeutic benefit of FAAH inhibition in dyslipidemia, liver steatosis, steatohepatitis, obesity, and metabolic syndrome (Steffens et al., *Nature,* 2005, 434, 782-6).

Osteoporosis is one of the most common degenerative diseases. It is characterized by reduced bone mineral density (BMD) with an increased risk for bone fractures. $CB_2$-deficient mice have a markedly accelerated age-related trabecular bone loss and cortical expansion. A $CB_2$-selective agonism enhances endocortical osteoblast number and activity and restrains trabecular osteoclastogenesis and attenuates ovariectomy-induced bone loss (Ofek et al., *Proc. Natl. Acad. Sci. U.S.A.* 2006, 103, 696-701). There is a substantial genetic contribution to BMD, although the genetic factors involved in the pathogenesis of human osteoporosis are largely unknown. The applicability to human BMD is suggested by genetic studies in which a significant association of single polymorphisms and haplotypes was found encompassing the CNR2 gene on human chromosome 1p36, demonstrating a role for the peripherally expressed $CB_2$ receptor in the etiology of osteoporosis (Karsak et al., *Hum. Mol. Genet,* 2005, 14, 3389-96).

Thus, small-molecule FAAH inhibitors should be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

A number of heteroaryl-substituted ureas have been reported in various publications. Certain substituted thiophene ureas are described in U.S. Pat. No. 6,881,741. Certain ureido-pyrazoles are described in U.S. Pat. No. 6,387,900. Certain benzothiazole amide derivatives are described in US Patent Publication US 2003/149036. Certain ureas are reported as prenyltransferase inhibitors in WO 2003/047569. Piperidinyl ureas are described as histamine $H_3$ receptor antagonists in U.S. Pat. No. 6,100,279. Piperazinyl ureas are disclosed as calcitonin mimetics in U.S. Pat. Nos. 6,124,299 and 6,395,740. Various ureas are reported as small-molecule FAAH modulators in US Patent Publication Nos. US 2006/173184 and US 2007/0004741, in Intl. Patent Appl. Nos. WO 2008/023720, WO 2008/047229, and WO 2008/024139, and by Cravatt et al. (Biochemistry 2007, 46(45), 13019. Ureas are described as modulators of other targets in U.S. Pat. Appl. Publ. US 2007/270433, and in Intl. Pat. Appl. Publ. Nos. WO 2007/096251 and WO 2006/085108. Certain piperidinyl ureas and piperazinyl ureas have been previously described as FAAH modulators in U.S. Pat. Appl. No. 60/931,920, filed May 25, 2007. However, there remains a desire for potent FAAH modulators with suitable pharmaceutical properties.

SUMMARY OF THE INVENTION

Certain heteroaryl-substituted piperidinyl urea derivatives have been found to have FAAH-modulating activity. Thus, the invention is directed to the general and preferred embodiments defined, respectively, by the independent and dependent claims appended hereto, which are incorporated by reference herein.

In one general aspect, the invention is directed to a chemical entity of Formula (I):

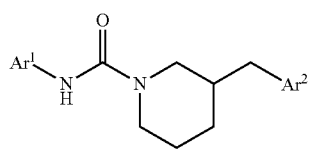

(I)

$Ar^1$ is mono- or fused bicyclic heteroaryl group consisting of 5-10 ring atoms and having one heteroatom selected from the group consisting of N, O and S, with a carbon atom as point of ring attachment, and optionally having up to four additional carbon ring atoms replaced with nitrogen, said heteroaryl group having not more than five heteroatoms, each heteroaryl group independently unsubstituted or substituted with halo, —$C_{1-4}$alkyl, —$OC_{1-4}$alkyl, —$OCF_3$, —CN, or —$CF_3$;

$Ar^2$ is
(i) phenyl unsubstituted or substituted with one or two $R^a$ moieties;
  where each $R^a$ moiety is independently —$C_{1-8}$alkyl, —$OC_{1-8}$alkyl, halo, —$CF_3$, —$OCF_3$, —$OCH_2CF_3$, —$S(O)_{0-2}C_{1-8}$alkyl, —$S(O)_{0-2}CF_3$, —$CO_2H$, —$N(R^b)R^c$, —$SO_2NR^bR^c$, —$NR^bSO_2R^c$, —$C(O)NR^bR^c$, or —$NO_2$;
  or two adjacent $R^a$ moieties taken together form —$O(CH_2)_{1-2}O$— or —$OCF_2O$—;
  where $R^b$ and $R^c$ are each independently —H or —$C_{1-8}$alkyl, or optionally $R^b$ and $R^c$ taken together with the atoms of attachment form a 4-8 membered ring;
(ii) phenyl substituted at the 3- or 4-position with -L-$Ar^3$, unsubstituted or substituted with one or two $R^a$ moieties, wherein:
  L is a linker selected from the group consisting of —$(CH_2)_{1-6}$—, —CH═CH—, —O—, —$C_{1-6}$alkyl-O—$C_{1-6}$alkyl-, —$C_{1-6}$alkyl-N($C_{1-6}$alkyl)-$C_{1-6}$alkyl-, —$C_{1-6}$alkyl-S(O)$_{0-2}C_{1-6}$alkyl-, —C≡C—, —C(O)—, or a covalent bond;
$Ar^3$ is:
  (a) phenyl unsubstituted or substituted with one or two $R^a$ moieties;

(b) a monocyclic heteroaryl group unsubstituted or substituted with one or two $R^a$ moieties; or
  (c) a 9- or 10-membered fused bicyclic heteroaryl group unsubstituted or substituted with one or two $R^a$ moieties; or
(iii) a 9- or 10-membered fused bicyclic heteroaryl having one heteroatom selected from the group consisting of N, O, and S, and optionally having up to four additional carbon ring atoms replaced with nitrogen, said fused bicyclic heteroaryl having not more than five heteroatoms, and unsubstituted or substituted with one, two or three $R^a$ moieties;
and pharmaceutically acceptable salts, pharmaceutically acceptable prodrugs, and pharmaceutically active metabolites of such compounds. In especially preferred embodiments, the invention is directed to compounds described or exemplified in the detailed description below and their pharmaceutically acceptable salts.

In a further general aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I); and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of at least one chemical entity selected from compounds of Formula (I) and their pharmaceutically acceptable salts, pharmaceutically active prodrugs, and pharmaceutically active metabolites. In preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, and neuroinflammation.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

As used herein, the terms "including", "containing" and "comprising" are used in their open, non-limiting sense.

The term "alkyl" refers to a straight- or branched-chain alkyl group having from 1 to 12 carbon atoms in the chain.

Examples of alkyl groups include methyl (Me, which also may be structurally depicted by / symbol), ethyl (Et), n-propyl, isopropyl, butyl, isobutyl, sec-butyl, tert-butyl (tBu), pentyl, isopentyl, tert-pentyl, hexyl, isohexyl, and so on.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and so on.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

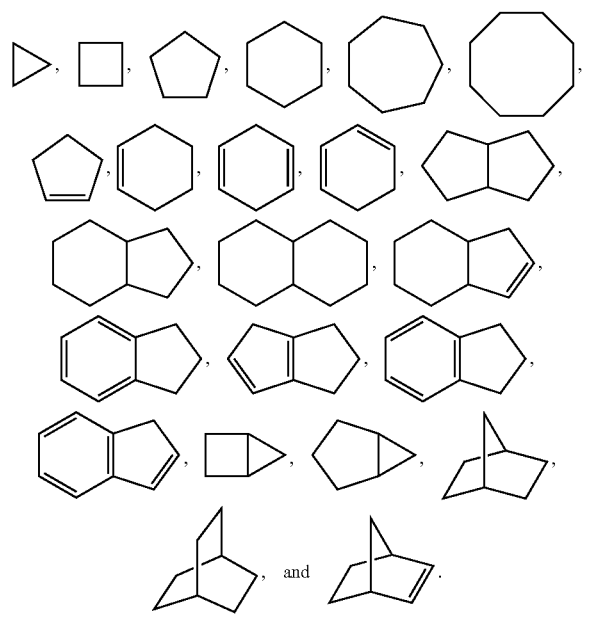

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples of heterocycloalkyl groups include the following entities, in the form of properly bonded moieties:

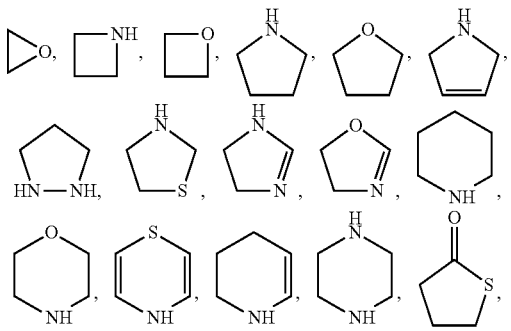

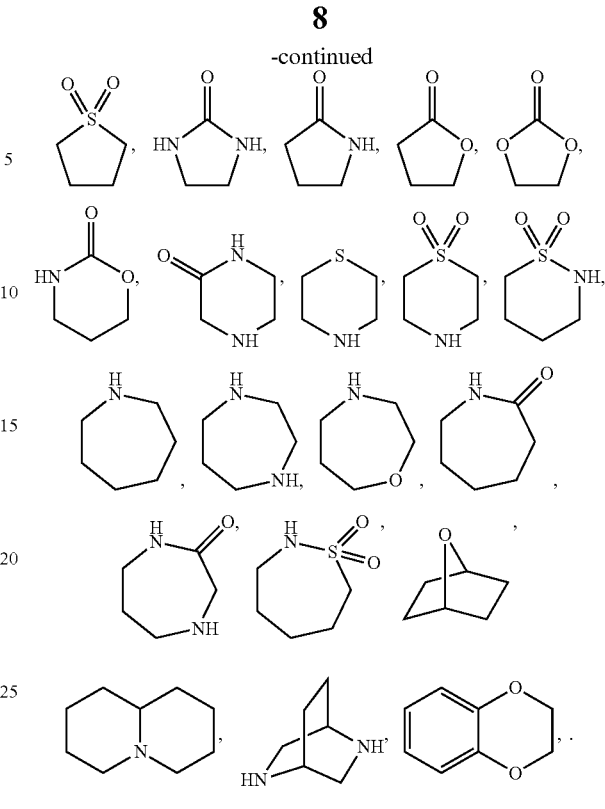

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

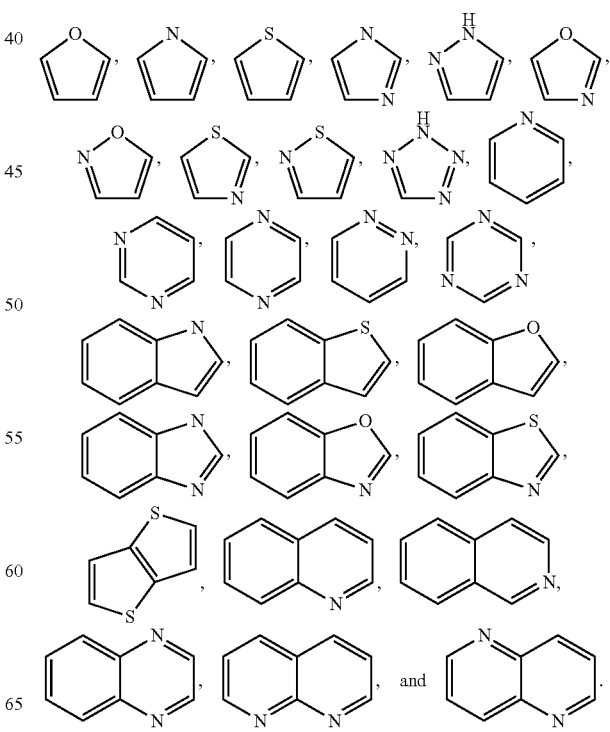

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

A structural formula given herein is intended to represent compounds having structures depicted by the formula as well as equivalent variations or forms. For example, compounds encompassed by Formula (I) may have asymmetric centers and therefore exist in different enantiomeric forms. All optical isomers and stereoisomers of the compounds of the general formula, and mixtures thereof, are considered within the scope of the formula. Thus, a general formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers (e.g. pyrazole, benzimidazole, tetrazole, or benzotriazole tautomers), or as atropisomers, which are intended to be represented by the structural formula. Additionally, a formula given herein is intended to embrace hydrates, solvates, and polymorphs of such compounds, and mixtures thereof.

A structural formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{32}$P, $^{33}$P, $^{35}$S, $^{18}$F, $^{36}$Cl, and $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)], including drug or substrate tissue distribution assays, or in radioactive treatment of patients. In particular, an $^{18}$F- or $^{11}$C-labeled compound may be preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a formula variable appears more than once, the choice of species from a specified list is independent of the choice of the species for the same variable elsewhere in the formula.

In certain embodiments, $Ar^1$ is isoxazolo[5,4-c]pyridin-3-yl, isoxazolo[4,5-c]pyridin-3-yl, isoxazolo[4,5-b]pyridin-3-yl, isoxazolo[5,4-b]pyridin-3-yl, imidazo[1,2-a]pyridin-8-yl, imidazo[1,2-a]pyridin-7-yl, imidazo[1,2-a]pyridin-6-yl, imidazo[1,2-a]pyridin-5-yl, imidazo[1,2-b]pyridazin-3-yl, imidazo[1,2-a]pyridin-3-yl, imidazo[1,2-a]pyridin-2-yl, imidazo[1,2-a]pyrimidin-7-yl, imidazo[1,2-a]pyrimidin-5-yl, imidazo[1,2-c]pyrimidin-7-yl, benzooxazol-6-yl, 1H-indazol-7-yl, quinolin-8-yl, isoquinolin-5-yl, isoquinolin-4-yl, 1,1-dioxo-1H-1$\lambda^6$-benzo[d]isothiazol-3-yl, 1H-pyrrolo[2,3-b]pyridin-5-yl, 1H-pyrrolo[2,3-b]pyridin-4-yl, 1H-pyrrolo[3,2-b]pyridin-6-yl, 2-methyl-benzothiazol-6-yl, 1-isopropyl-1H-pyrazolo[3,4-b]pyridin-5-yl, 2-methyl-benzooxazol-5-yl, 1H-indazol-7-yl, 1,3-dimethyl-1H-pyrazolo[3,4-b]pyridin-5-yl, 2-methyl-2H-indazol-4-yl, benzooxazole-2-yl group, 6-[1,2,3]triazol-1-yl-pyridin-3-yl, 6-[1,2,4]triazol-4-yl-pyridin-3-yl, 6-[1,2,4]triazol-1-yl-pyridin-3-yl, 6-[1,2,3]triazol-2-yl-pyridin-3-yl, 4-[1,2,3]triazol-2-yl-phenyl, 4-[1,2,3]triazol-1-yl-phenyl, 5-methyl-[1,3,4]oxadiazol-2-yl, 2-phenyl-pyrimidin-5-yl, 3-pyridyl, benzisoxazol-3-yl, pyrimidin-4-yl, isoxazol-3-yl, 6-fluorobenzo[d]isoxazol-3-yl, 3-phenyl-[1,2,4]thiadiazol-5-yl, 1H-tetrazol-5-yl, benzo[1,2,5]thiadiazol-4-yl, benzo[1,2,5]oxadiazol-4-yl, thiophen-2-yl, thiophen-3-yl, 6-chloro-pyridazin-3-yl, pyrazin-2-yl, 1H-benzotriazol-5-yl, [1,5]naphthyridin-2-yl, benzothiazol-6-yl, or 1H-pyrazol-3-yl. In certain embodiments, $Ar^1$ is pyrimidine, isoxazole, benzisoxazole, imidazo[1,2-b]pyridazine, or pyridine, wherein each group is optionally substituted with one or two $R^a$ moieties.

In certain embodiments, $Ar^2$ is phenyl substituted with one or two $R^a$ moieties. In certain embodiments, $Ar^2$ is phenyl, substituted with one or two $R^a$ moieties wherein each wherein each $R^a$ moiety is independently selected from the group consisting of: chloro, cyano, isobutyl, methylsulfanyl, methanesulfonyl, trifluoromethyl, trifluoromethoxy, 2,2,2-trifluoroethoxy, fluoro, methyl, methoxy, tert-butyl, bromo, methoxycarbonyl, cyanomethyl, methoxycarbonylmethyl, trifluoromethanesulfonyl, trifluoromethanesulfanyl, and butyl; or two adjacent $R^a$ moieties taken together form —OCH$_2$O— or —OCF$_2$O—. In further embodiments, each $R^a$ moiety is independently selected from the group consisting of: F, Cl, Br, CF$_3$, or two adjacent $R^a$ moieties taken together form —OCF$_2$O—.

In certain embodiments, $Ar^2$ is phenyl substituted at the 3- or 4-position with -L-Ar$^3$, unsubstituted or substituted with one or two $R^a$ moieties. In further embodiments, $Ar^2$ is phenyl substituted at the 3- or 4-position with -L-Ar$^3$, unsubstituted or substituted with one or two $R^a$ moieties and wherein L is —CH$_2$CH$_2$—, —O—, —OCH$_2$—, or —C≡C—. In further embodiments, L is —O—. In further embodiments, L is phenyl, unsubstituted or substituted with one or two $R^a$ moieties and each $R^a$ moiety is independently selected from the group consisting of: chloro, cyano, isobutyl, methylsulfanyl, methanesulfonyl, trifluoromethyl, trifluoromethoxy, 2,2,2-trifluoroethoxy, fluoro, methyl, methoxy, tert-butyl, bromo, methoxycarbonyl, cyanomethyl, methoxycarbonylmethyl, trifluoromethanesulfonyl, trifluoromethanesulfanyl, and butyl; or two adjacent $R^a$ moieties taken together form —OCH$_2$O— or —OCF$_2$O—. In certain preferred embodiments, each $R^a$ moiety is independently fluoro.

In a further embodiment, $Ar^2$ is a 9- or 10-membered fused bicyclic heteroaryl having one heteroatom selected from the group consisting of N, O, and S, and optionally having up to four additional carbon ring atoms replaced with nitrogen, said fused bicyclic heteroaryl having not more than five heteroatoms, and unsubstituted or substituted with one, two or three $R^a$ moieties. In one embodiment, $Ar^2$ is a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two or three $R^a$ moieties. In still further preferred embodiments, $Ar^2$ is a benzimidazolyl, indazolyl, benzothiophenyl, quinolinyl, indolyl, or benzofuranyl group. In a further embodiment $Ar^2$ is quinolinyl.

The invention also relates to pharmaceutically acceptable salts of the free acids or bases represented by compounds in Table 1, preferably of the preferred embodiments described above and of the specific compounds exemplified herein. The therapeutic compositions and methods of the invention may employ pharmaceutically acceptable salts of the free acids or bases represented by compounds in Table 1, preferably of the preferred embodiments described above and of the specific compounds exemplified herein. A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002.

Preferred pharmaceutically acceptable salts are those that are pharmacologically effective and suitable for contact with the tissues of patients without undue toxicity, irritation, or allergic response. A compound from Table 1 may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound in Table 1 contains a basic nitrogen, the desired pharmaceutically acceptable salt may be prepared by any suitable method available in the art, for example, by treatment of the free base with an inorganic acid, such as hydrochloric acid, hydrobromic acid, sulfuric acid, sulfamic acid, nitric acid, boric acid, phosphoric acid, and the like; or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid; an amino acid, such as aspartic acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, or ethanesulfonic acid; or any compatible mixture of acids such as those given as examples herein.

If the compound in Table 1 is an acid such as a carboxylic acid or sulfonic acid, the desired pharmaceutically acceptable salt may be prepared by any suitable method, for example, by treatment of the free acid with an inorganic or organic base, such as an amine (primary, secondary or tertiary), an alkali metal hydroxide, alkaline earth metal hydroxide, or any compatible mixture of bases such as those given as examples herein. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Table 1. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Table 1). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of compounds of Table 1 as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Table 1. A "pharmaceutically active metabolite" means a pharmacologically active product of metabolism in the body of a compound of Table 1 or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Table 1, and their pharmaceutically acceptable salts, pharmaceutically acceptable prodrugs, and pharmaceutically active metabolites (collectively, "active agents") of the present invention are useful as FAAH inhibitors in the methods of the invention. The active agents may be used in the inventive methods for the treatment of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Exemplary medical conditions, diseases, and disorders mediated by FAAH activity include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, diabetes, metabolic syndrome and osteoporosis.

Thus, the active agents may be used to treat subjects diagnosed with or suffering from such a disease, disorder, or condition. The term "treat" or "treating" as used herein is intended to refer to administration of an agent or composition of the invention to a subject for the purpose of effecting a therapeutic benefit through modulation of FAAH activity. Treating includes reversing, ameliorating, alleviating, inhibiting the progress of, lessening the severity of, reducing the incidence of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, movement disorders (e.g., multiple sclerosis), energy metabolism (e.g. insulin resistance, diabetes, dyslipidemia, liver steatosis, steatohepatitis, obesity, and metabolic syndrome) and bone homeostasis (e.g. osteoporosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent, in one example herein a FAAH-inhibiting agent, according to the invention include cancer pain, post-operative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. A "therapeutically effective amount" or "effective amount" means an amount or dose of a FAAH-modulating agent sufficient to generally bring about a therapeutic benefit in patients in need of treatment for a disease, disorder, or condition mediated by FAAH activity. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.0001 to about 200 mg of active agent per kg of subject's body weight per day, preferably about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease, disorder, or condition has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 5 mg to 5 g daily, or from about 50 mg to 5 g daily, in single or divided doses. For example, a total daily dosage of about 5 mg to 5 g daily may be accomplished by dosing once, twice, three, or four times per day.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary active agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

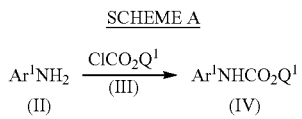

Referring to Scheme A, a carbamate of formula (IV) may be obtained by reacting a compound of formula (II) with a compound of formula (III), in which $Q^1$ represents an aryl group, under chloroformate condensation conditions. Preferably, $Q^1$ is substituted or unsubstituted phenyl, and the reaction occurs with or without a base, in a solvent such as acetonitrile, at a temperature from about 0° C. to about 80° C. More preferably, $Q^1$ is phenyl, and the reaction occurs in pyridine at room temperature ("rt"), or in acetonitrile at 50° C. without added base.

SCHEME B

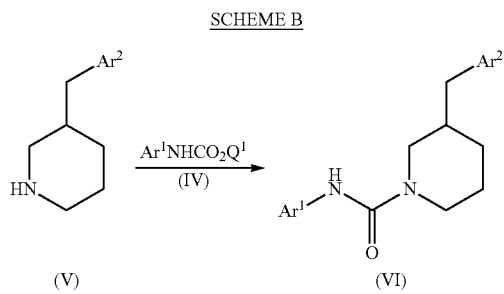

Referring to Scheme B, a compound of formula (VI) is obtained by reacting a compound of formula (V) with a compound of formula (IV) under aryl carbamate condensation conditions. The reaction may preferably take place in a solvent at a temperature from about rt to about 120° C. Preferably, $Q^1$ is phenyl, and the reaction is performed in dimethylsulfoxide (DMSO) in a microwave reactor at about 100° C. or by conventional heating from about rt to about 50° C.

SCHEME C

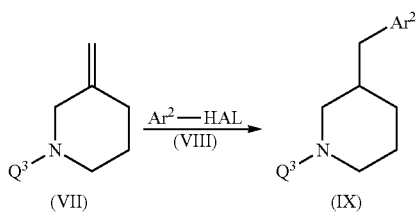

Intermediate compounds of formula (IX) are prepared according to Scheme C. Hydrometallation of an alkenyl compound (VII) gives an activated species, which is subsequently reacted with a suitable reagent $Ar^2$-HAL (where HAL is chloride, bromide, or iodide) to provide a compound (IX). Preferably, hydrometallation is accomplished by hydroboration using a suitable dialkylborane reagent such as 9-borabicyclo[3.3.1]nonane (9-BBN) or diisopinocampheylborane, in a solvent such as THF. The resulting boron adduct is preferably reacted with compounds of formula (VIII) in the presence of a suitable palladium catalyst, a base such as $K_2CO_3$ or $Cs_2CO_3$, in a solvent such as N,N-dimethylformamide (DMF) or an aqueous mixture thereof. When $Q^3$ is a suitable protecting group, then compounds of formula (IX) can be converted into compounds of formula (V) using suitable deprotection conditions.

Compounds of Table 1 may be converted to their corresponding salts by applying general techniques described in the art. For example, a compound of Table 1 may be treated with trifluoroacetic acid, HCl, or citric acid in a solvent such as $Et_2O$, 1,4-dioxane, dichloromethane (DCM), tetrahydrofuran (THF), or MeOH to provide the corresponding salt forms.

Compounds prepared according to the schemes described above may be obtained as single enantiomers, diastereomers, or regioisomers, by enantio-, diastero-, or regio-specific synthesis, or by resolution. Compounds prepared according to the schemes above may alternatively be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry:

In preparing the examples listed below, the following general experimental and analytical methods were used.

Reaction mixtures were stirred under a nitrogen atmosphere at rt unless otherwise noted. Where solutions or mixtures are concentrated, they are typically concentrated under reduced pressure using a rotary evaporator. Where solutions are dried, they are typically dried over a drying agent such as $MgSO_4$ or $Na_2SO_4$, unless otherwise noted.

Microwave reactions were carried out in either a CEM Discover® or a Biotage Initiator™ Microwave at specified temperatures.

Normal phase flash column chromatography (FCC) was performed on silica gel columns using ethyl acetate (EtOAc)/hexanes as eluent, unless otherwise indicated.

Reversed-Phase High Performance Liquid Chromatography (HPLC) was performed using: Shimadzu instrument with a Phenomenex Gemini column 5 µm C18 (150×21.2 mm) or Waters Xterra RP18 OBD column 5 µm (100×30 mm), a gradient of 95:5 to 0:100 water (0.05% TFA)/$CH_3CN$ (0.05% TFA), a flow rate of 80 mL/min, and detection at 254 nM.

Mass spectra were obtained on an Agilent series 1100 MSD using electrospray ionization (ESI) in positive mode unless otherwise indicated.

NMR spectra were obtained on either a Bruker model DPX400 (400 MHz), DPX500 (500 MHz) or DRX600 (600 MHz) spectrometer. The format of the $^1$H NMR data below is: chemical shift in ppm down field of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1: Isoxazolo[5,4-c]pyridin-3-ylamine

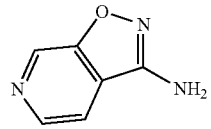

To a solution of 3-chloro-isonicotinitrile (1.13 g, 8.36 mmol) in DMF (6.0 mL) were added potassium carbonate (1.69 g, 12.2 mmol) and acetohydroxamic acid (0.91 g, 12.2 mmol). The reaction mixture was stirred at rt overnight, diluted with EtOAc (200 mL) and extracted with saturated aqueous NaHCO$_3$ (200 mL) then saturated aqueous NaCl (100 mL). The aqueous layers were back extracted with EtOAc (200 mL) and the combined organic layers were dried (MgSO$_4$) and concentrated. The crude residue was purified (FCC, 2 N NH$_3$ in MeOH/DCM) to give isoxazolo[5,4-c]pyridin-3-ylamine (0.447 g, 41%). MS (ESI$^+$): calcd for C$_6$H$_5$N$_3$O m/z 135.04, found 136.2 (M+H)$^+$. $^1$H NMR (d$_6$-DMSO): 8.93 (d, J=0.8, 1H), 8.45 (d, J=5.2, 1H), 7.88-7.86 (dd, J=5.2, 1.2, 1H), 6.72 (br s, 2H).

Intermediates 2 and 3 were prepared using methods analogous to those described for intermediate 1 with the stated changes to reagents described below.

Intermediate 2: Isoxazolo[4,5-c]pyridin-3-ylamine

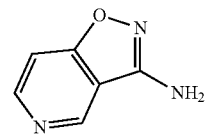

The title compound was prepared using methods analogous to those described for intermediate 1 except 4-chloro-3-cyanopyridine was the starting material. MS (ESI$^+$): calcd for C$_6$H$_5$N$_3$O m/z 135.04, found 136.2 (M+H)$^+$. $^1$H NMR (d$_6$-DMSO): 9.09 (d, J=1.0, 1H), 8.57 (d, J=5.9, 1H), 7.53 (dd, J=5.9, 1.0, 1H), 6.77 (br s, 2H).

Intermediate 3: Isoxazolo[4,5-b]pyridin-3-ylamine

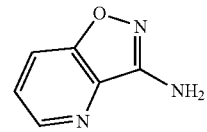

The title compound was prepared using methods analogous to those described for intermediate 1 except 3-chloro-2-cyanopyridine was the starting material. MS (ESI$^+$): calcd for C$_6$H$_5$N$_3$O m/z 135.04, 136.2 (M−H)$^+$. $^1$H NMR (d$_6$-DMSO): 8.58 (dd, J=4.5, 1.1, 1H), 7.98 (dd, J=8.5, 1.1, 1H), 7.57 (dd, J=8.5, 4.5, 1H), 6.55 (br s, 2H).

Intermediate 4: Imidazo[1,2-a]pyridin-8-ylamine

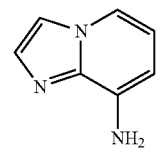

To a solution of 50% aqueous chloroacetaldehyde (4.14 mL, 32.6 mmol) were added sodium bicarbonate (3.19 g, 40.0 mmol) and 2,3-diaminopyridine (3.56 g, 32.6 mmol). The reaction mixture was stirred at rt overnight, then diluted with saturated aqueous NaCl (100 mL) and extracted with n-butanol (3×200 mL). The organic layers were combined, dried (MgSO$_4$), and concentrated. The crude residue was purified (FCC, 2 N NH$_3$ in MeOH/DCM) to give imidazo[1,2-a]pyridin-8-ylamine (2.18 g, 51%). MS (ESI$^+$): calcd for C$_7$H$_7$N$_3$ m/z 133.06, found 134.1 (M+H)$^+$. $^1$H NMR (d$_6$-DMSO): 7.79-7.75 (m, 2H), 7.40 (d, J=1.1, 1H), 6.60 (s, 1H), 6.21 (dd, J=7.3, 1.1, 1H), 5.53 (br s, 2H).

Intermediate 5: Imidazo[1,2-a]pyridin-7-ylamine

Intermediate 5 was prepared using methods analogous to those described for intermediate 4 except 2,4-diaminopyridine was the starting material. MS (ESI$^+$): calcd for C$_7$H$_7$N$_3$ m/z 133.06, found 134.1 (M+H)$^+$. $^1$H NMR (d$_6$-DMSO): 8.13-8.10 (m, 1H), 7.48 (s, 1H), 7.15 (s, 1H), 6.36-6.33 (m, 2H), 5.52 (br s, 2H).

Intermediate 6: Imidazo[1,2-a]pyridin-5-ylamine

To a solution of 2,6-diaminopyridine (5.00 g, 45.8 mmol) in 1:1 H$_2$O:EtOH (10 mL) were added sodium bicarbonate (5.00 g, 59.5 mmol) and chloroacetaldehyde (4.31 g, 27.5 mmol). The reaction mixture was heated to 70° C. overnight, then cooled to rt, diluted with saturated aqueous NaCl (100 mL), and extracted with n-butanol (3×200 mL). The organic layers were combined, dried (MgSO$_4$), and concentrated. The crude residue was purified (FCC, 2 N NH$_3$ in MeOH/DCM) to give imidazo[1,2-a]pyridin-5-ylamine (1.32 g, 22%). MS (ESI$^+$): calcd for C$_7$H$_7$N$_3$ m/z 133.06, found 134.1 (M+H)$^+$. $^1$H NMR (d$_6$-DMSO): 8.23-8.21 (m, 1H), 7.91 (d, J=1.3, 1H), 7.50 (dd, J=8.8, 7.4, 1H), 7.22 (d, J=8.8, 1H), 6.97 (br s, 2H), 6.37 (dd, J=7.4, 0.9, 1H).

Intermediates 7 to 9 were prepared using methods analogous to those described for intermediate 6 with the stated changes to reagents described below.

Intermediate 7: Imidazo[1,2-a]pyrimidin-7-ylamine

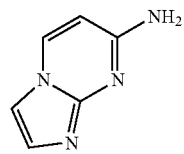

Intermediate 7 was prepared using methods analogous to those described for Intermediate 6 except 2,4-diaminopyrimidine was the starting material. MS (ESI+): calcd for $C_6H_6N_4$ m/z 134.06, found 135.1 (M+H)+. 1H NMR (d4-methanol): 8.27 (d, J=7.2, 1H), 7.31 (d, J=1.8, 1H), 7.18 (d, J=1.8, 1H), 6.35 (d, J=7.2, 1H).

Intermediate 8: Imidazo[1,2-a]pyrimidin-5-ylamine

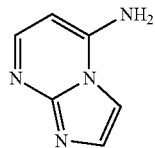

Intermediate 8 was prepared using methods analogous to those described for intermediate 6 except 2,4-diaminopyrimidine was the starting material. MS (ESI+): calcd for $C_6H_6N_4$ m/z 134.06, found 135.1 (M+H)+. 1H NMR (d4-methanol): 8.41 (d, J=5.4, 1H), 7.72 (d, J=1.8, 1H), 7.55 (d, J=1.8, 1H), 6.17 (d, J=5.4, 1H).

Intermediate 9: Imidazo[1,2-c]pyrimidin-7-ylamine

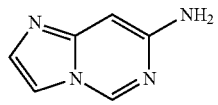

Intermediate 9 was prepared using methods analogous to those described for intermediate 6 except 4,6-diaminopyrimidine was the starting material. MS (ESI+): calcd for $C_6H_6N_4$ m/z 134.06, found 135.1 (M+H)+. 1H NMR (d6-DMSO): 9.80 (s, 1H), 8.39 (s, 1H), 8.03 (s, 1H), 7.01 (s, 1H), 6.90 (s, 2H).

Intermediates 10 to 18 were prepared by treatment of the appropriate aminoheterocycle intermediate with 1 equivalent of phenylchloroformate in dry $CH_3CN$ and 1 equivalent of pyridine. The reagents were stirred at rt for 4 h, diluted with EtOAc, washed with $NaHCO_3$, and dried over $MgSO_4$. The material was purified by FCC to provide pure phenyl carbamate intermediates.

Intermediate 10: Imidazo[1,2-a]pyridin-8-yl-carbamic acid phenyl ester

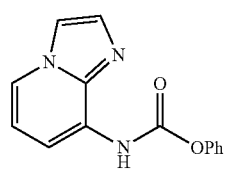 [SMILES: O=C(Nc1cccn2ccnc12)Oc1ccccc1]

MS (ESI+): calcd for $C_{14}H_{11}N_3O_2$ m/z 253.09, found 254.1 (M+H)+.

Intermediate 11: Imidazo[1,2-a]pyridin-3-yl-carbamic acid phenyl ester

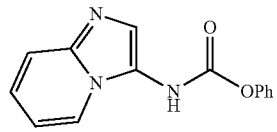 [SMILES: O=C(Nc1cnc2ccccn12)Oc1ccccc1]

MS (ESI+): calcd for $C_{14}H_{11}N_3O_2$ m/z 253.09, found 254.1 (M+H)+.

Intermediate 12: Imidazo[1,2-a]pyridin-2-yl-carbamic acid phenyl ester

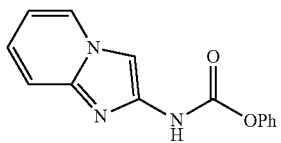 [SMILES: O=C(Nc1cn2ccccc2n1)Oc1ccccc1]

MS (ESI+): calcd for $C_{14}H_{11}N_3O_2$ m/z 253.09, found 254.1 (M+H)+.

Intermediate 13: (1H-Indazol-7-yl)-carbamic acid phenyl ester

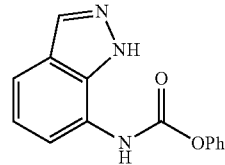

MS (ESI+): calcd for $C_{14}H_{11}N_3O_2$ m/z 253.09, found 254.3 (M+H)+.

Intermediate 14: Quinolin-8-yl-carbamic acid phenyl ester

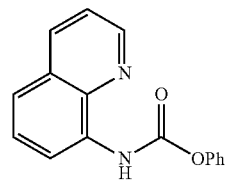 [SMILES: O=C(Nc1cccc2cccnc12)Oc1ccccc1]

MS (ESI+): calcd for $C_{16}H_{12}N_2O_2$ m/z 264.09, found 265.1 (M+H+).

Intermediate 15: Isoquinolin-5-yl-carbamic acid phenyl ester

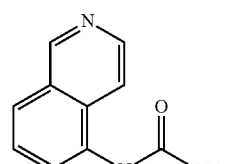

MS (ESI+): calcd for $C_{16}H_{12}N_2O_2$ m/z 264.09, found 265.1 (M+H)+.

Intermediate 16: Isoquinolin-4-yl-carbamic acid phenyl ester

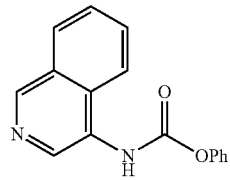 [SMILES: O=C(Nc1cncc2ccccc12)Oc1ccccc1]

MS (ESI⁺): calcd for $C_{16}H_{12}N_2O_2$ m/z 264.09, found 265.1 (M+H)⁺.

Intermediate 17: (1H-Pyrrolo[2,3-b]pyridin-4-yl)-carbamic acid phenyl ester

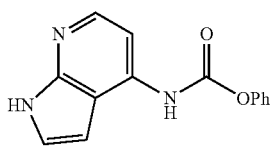

MS (ESI⁺): calcd for $C_{14}H_{11}N_3O_2$ m/z 253.09, found 254.1 (M+H)⁺.

Intermediate 18: (1H-Pyrrolo[3,2-b]pyridin-6-yl)-carbamic acid phenyl ester

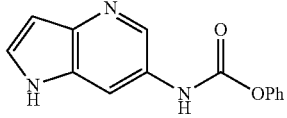 [SMILES: O=C(Nc1cnc2cc[nH]c2c1)Oc1ccccc1]

MS (ESI⁺): calcd for $C_{14}H_{11}N_3O_2$ m/z 253.09, found 254.1 (M+H)⁺.

Intermediate 19: Imidazo[1,2-b]pyridazin-3-yl-carbamic acid phenyl ester

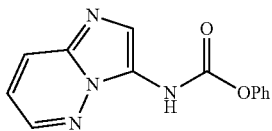 [SMILES: O=C(Nc1cnc2cccnn12)Oc1ccccc1]

To a solution of imidazo[1,2-b]pyridazin-3-ylamine (209 mg, 1.56 mmol) in dry DMF (5.0 mL) was added pyridine (382 µL, 4.68 mmol) and phenyl chloroformate (244 mg, 1.56 mmol). After 3 h at rt, the mixture was diluted with EtOAc (100 mL) and washed with saturated aqueous NaHCO₃ (50 mL). The organic layer was dried (MgSO₄) and concentrated. The residue was purified (FCC) to give imidazo[1,2-b]pyridazin-3-yl-carbamic acid phenyl ester (285 mg, 72%). MS (ESI⁺): calcd for $C_{13}H_{10}N_4O_2$ m/z 254.08, found 255.3 (M+H)⁺.

Intermediate 20: Isoxazolo[5,4-c]pyridin-3-yl-carbamic acid phenyl ester

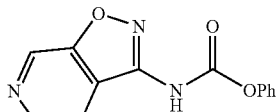

To a suspension of isoxazolo[5,4-c]pyridin-3-ylamine (1.49 g, 11.0 mmol) in CH₃CN (50 mL) was added phenyl chloroformate (0.696 mL, 5.50 mmol). The reaction mixture was heated at 70° C. overnight, then cooled to rt, diluted with H₂O (100 mL) and saturated aqueous NaHCO₃ (10 mL). The resulting yellow precipitate was filtered and dried under vacuum to give isoxazolo[5,4-c]pyridin-3-yl-carbamic acid phenyl ester (1.099 g, 39%). MS (ESI⁺): calcd for $C_{13}H_9N_3O_3$ m/z 255.06, found 256.1 (M+H)⁺.

Intermediates 21 to 23 were prepared using methods analogous to those described for Intermediate 20.

Intermediate 21: Isoxazolo[5,4-b]pyridin-3-yl-carbamic acid phenyl ester

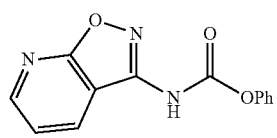 [SMILES: O=C(Nc1noc2ncccc12)Oc1ccccc1]

MS (ESI⁺): calcd for $C_{13}H_9N_3O_3$ m/z 255.06, found 256.1 (M+H)⁺.

Intermediate 22: Isoxazolo[4,5-c]pyridin-3-yl-carbamic acid phenyl ester

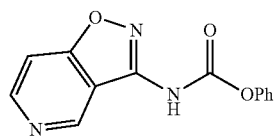 [SMILES: O=C(Nc1noc2ccncc12)Oc1ccccc1]

MS (ESI⁺): calcd for $C_{13}H_9N_3O_3$ m/z 255.06, found 256.1 (M+H)⁺.

Intermediate 23: Isoxazolo[4,5-b]pyridin-3-yl-carbamic acid phenyl ester

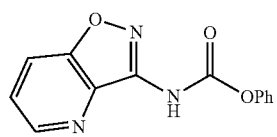 [SMILES: O=C(Nc1noc2cccnc12)Oc1ccccc1]

MS (ESI⁺): calcd for $C_{13}H_9N_3O_3$ m/z 255.06, found 256.1 (M+H)⁺.

Example 1

3-(2,2-Difluoro-benzo[1,3]dioxol-5-ylmethyl)-piperidine-1-carboxylic acid pyridin-3-ylamide

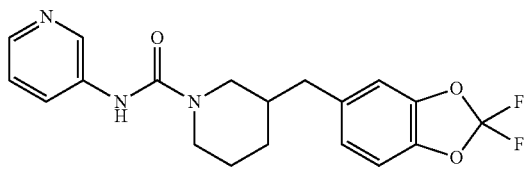 [SMILES: O=C(Nc1cccnc1)N1CCCC(Cc2ccc3c(c2)OC(F)(F)O3)C1]

Step A: 3-(2,2-Difluoro-benzo[1,3]dioxol-5-ylmethyl)-piperidine-1-carboxylic acid tert-butyl ester. 1-Boc-3-methylene piperidine (842 mg, 4.27 mmol) was degassed (neat) for 15 minutes and then treated with a THF solution of 9-BBN (0.5 M in THF, 8.6 mL, 4.3 mmol). The reaction mixture was refluxed for 2 h, then cooled to rt. The reaction mixture was then added, via cannula, to a preformed solution of 5-bromo-2,2-difluoro-1,3-benzodioxole (1.00 g, 4.22 mmol), Pd(dppf)Cl$_2$—CH$_2$Cl$_2$ (94 mg, 0.128 mmol), and potassium carbonate (746 mg, 5.40 mmol) in DMF/H$_2$O (10 mL/1 mL). The resultant mixture was heated at 60° C. for 18 h, cooled to rt, poured into water, basified to pH 11 with 1 N NaOH, and extracted with EtOAc (3×). The organic layers were combined, dried (Na$_2$SO$_4$), and concentrated. The crude residue was purified (FCC) to give 3-(2,2-difluoro-benzo[1,3]dioxol-5-ylmethyl)-piperidine-1-carboxylic acid tert-butyl ester (1.00 g, 67%).

Step B: 3-[(2,2-Difluoro-1,3-benzodioxol-5-yl)methyl]-piperidine hydrochloride. To a solution of 3-(2,2-difluoro-benzo[1,3]dioxol-5-ylmethyl)-piperidine-1-carboxylic acid tert-butyl ester (1.0 g, 2.8 mmol) in CH$_2$Cl$_2$ (11 mL) was added HCl (4 M in dioxane, 4.2 mL, 16.9 mmol). The reaction mixture was stirred at r.t. overnight and then concentrated to give 3-[(2,2-difluoro-1,3-benzodioxol-5-yl)methyl]-piperidine as the hydrochloride salt (791 mg, 96%). The crude product was used without further purification.

Step C: 3-(2,2-Difluoro-benzo[1,3]dioxol-5-ylmethyl)-piperidine-1-carboxylic acid pyridin-3-ylamide. To a solution of 3-[(2,2-difluoro-1,3-benzodioxol-5-yl)methyl]-piperidine hydrochloride (100 mg, 0.34 mmol) in CH$_3$CN (2 mL) was added Et$_3$N (0.07 mL, 0.52 mmol). To this reaction mixture, pyridin-3-yl-carbamic acid phenyl ester (77.0 mg, 1.05 mmol) was added and the reaction mixture was heated overnight at 35° C. The reaction mixture was then concentrated and the crude residue was purified (FCC, 2 N NH$_3$ in MeOH/DCM) to give 3-(2,2-difluoro-benzo[1,3]dioxol-5-ylmethyl)-piperidine-1-carboxylic acid pyridin-3-ylamide (120 mg, 93%). MS (ESI$^+$): calcd for C$_{19}$H$_{19}$F$_2$N$_3$O$_3$ m/z 375.14, found 376.2 (M+H)$^+$. $^1$H NMR (d$_4$-methanol): 8.54 (d, J=2.3, 1H), 8.17-8.13 (m, 1H), 7.86 (ddd, J=8.4, 2.6, 1.4, 1H), 7.34-7.30 (m, 1H), 7.10-7.06 (m, 2H), 6.99 (dd, J=8.2, 1.5, 1H), 4.05-3.95 (m, 2H), 3.04-2.98 (m, 1H), 2.74-2.64 (m, 2H), 2.58-2.53 (m, 1H), 1.86-1.74 (m, 3H), 1.56-1.47 (m, 1H), 1.30-1.22 (m, 1H).

The compounds in Examples 2 to 9 were prepared using methods analogous to those described in Example 1.

Example 2

N-Pyrimidin-4-yl-3-{[4-(trifluoromethyl)phenyl]methyl}piperidine-1-carboxamide

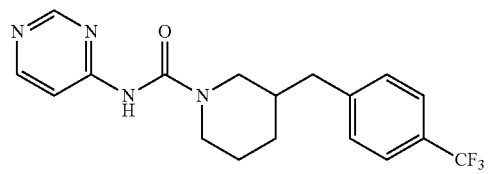 [SMILES: O=C(Nc1ccncn1)N1CCCC(Cc2ccc(C(F)(F)F)cc2)C1]

$^1$H NMR (d$_4$-methanol): 8.76 (d, J=1.0, 1H), 8.53 (d, J=6.0, 1H), 8.00 (dd, J=1.5, 6.0, 1H), 7.57 (d, J=8.0, 2H), 7.37 (br s, 1H), 7.28 (d, J=8.0, 2H), 4.04 (d, J=12.5, 1H), 3.90 (d, J=12.5, 1H), 3.75-3.02 (m, 1H), 2.74-2.70 (m, 2H), 2.56 (dd, J=8, 13.5, 1H), 1.96-1.75 (m, 3H), 1.57-1.47 (m, 1H), 1.30-1.18 (m, 1H).

Example 3

N-Pyrimidin-4-yl-3-{[3-(trifluoromethyl)phenyl]methyl}piperidine-1-carboxamide

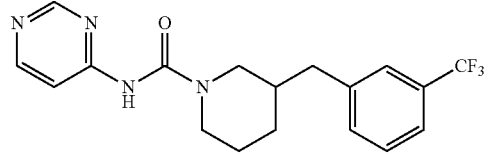 [SMILES: O=C(Nc1ccncn1)N1CCCC(Cc2cccc(C(F)(F)F)c2)C1]

MS (ESI$^+$): calcd for C$_{18}$H$_{19}$F$_3$N$_4$O m/z 364.15, found 365.2 (M+H)$^+$. $^1$H NMR (CDCl$_3$): 8.76 (d, J=1.0, 1H), 8.53 (d, J=5.5, 1H), 8.00 (dd, J=1.5, 6.0, 1H), 7.50 (d, J=7.5, 1H), 7.43-7.42 (m, 2H), 7.38-7.35 (m, 2H), 4.04 (d, J=12.5, 1H), 3.90 (d, J=12.5, 1H), 3.07-3.01 (m, 1H), 2.76-2.70 (m, 2H), 2.56 (dd, J=8.0, 13.5, 1H), 1.97-1.75 (m, 3H), 1.57-1.46 (m, 1H), 1.29-1.19 (m, 1H).

Example 4

3-[4(4-Fluorophenyl)methyl]-N-pyrimidin-4-ylpiperidine-1-carboxamide

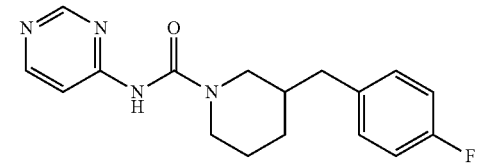 [SMILES: O=C(Nc1ccncn1)N1CCCC(Cc2ccc(F)cc2)C1]

$^1$H NMR (CDCl$_3$): 8.76 (d, J=1.0, 1H), 8.52 (d, J=6.0, 1H), 8.00 (dd, J=1.0, 6.0, 1H), 7.40 (br s, 1H), 7.11-7.10 (m, 2H), 7.01-6.97 (m, 2H), 3.99 (d, J=12.5, 1H), 3.91 (d, J=12.5, 1H), 3.04-2.99 (m, 1H), 2.69-2.63 (m, 2H), 2.62 (dd, J=6.5, 14.0, 1H), 2.49 (dd, J=7.5, 14.0, 1H), 1.87-1.71 (m, 3H), 1.56-1.44 (m, 1H), 1.29-1.14 (m, 1H).

Example 5

N-1,2-Benzisoxazol-3-yl-3-{[4-(trifluoromethyl)-phenyl]-methyl}-piperidine-1-carboxamide

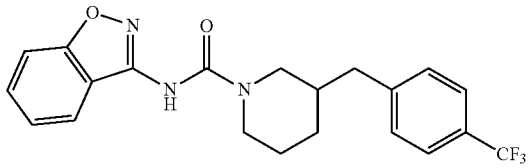 [SMILES: O=C(Nc1noc2ccccc12)N1CCCC(Cc2ccc(C(F)(F)F)cc2)C1]

$^1$H NMR (CDCl$_3$): 9.04 (s, 1H), 8.05 (d, J=8.5, 1H), 7.58-7.54 (m, 3H), 7.45 (d, J=8.5, 1H), 7.33-7.28 (m, 3H), 4.21-4.14 (m, 2H), 3.09-3.05 (m, 1H), 2.84-2.75 (m, 2H), 2.56 (dd, J=8.0, 13.5, 1H), 1.99-1.91 (m, 1H), 1.88-1.76 (m, 2H), 1.64-1.50 (m, 1H), 1.30-1.17 (m, 1H).

Example 6

N-1,2-Benzisoxazol-3-yl-3-{[3-(trifluoromethyl)-phenyl]-methyl}-piperidine-1-carboxamide

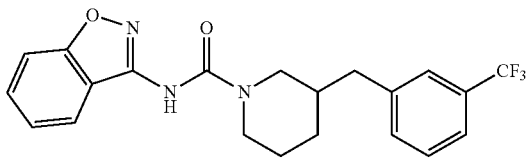 [SMILES: O=C(Nc1noc2ccccc12)N1CCCC(Cc2cccc(C(F)(F)F)c2)C1]

MS (ESI$^+$): calcd for C$_{21}$H$_{20}$F$_3$N$_3$O$_2$ m/z 403.15, found 404.2 (M+H)$^+$. $^1$H NMR (CDCl$_3$): 9.02 (s, 1H), 8.06 (d, J=8.5, 1H), 7.57-7.54 (m, 1H), 7.48-7.45 (m, 3H), 7.41-7.36 (m, 2H), 7.31-7.28 (m, 1H), 4.20 (d, J=10.5, 1H), 4.15 (d, J=11.5, 1H), 3.10-3.05 (m, 1H), 2.83-2.79 (m, 2H), 2.55 (dd, J=8.5, 13.5, 1H), 1.99-1.90 (m, 1H), 1.87-1.77 (m, 2H), 1.64-1.51 (m, 1H), 1.29-1.17 (m, 1H).

Example 7

N-1,2-Benzisoxazol-3-yl-3-[(4-fluorophenyl)methyl]piperidine-1-carboxamide

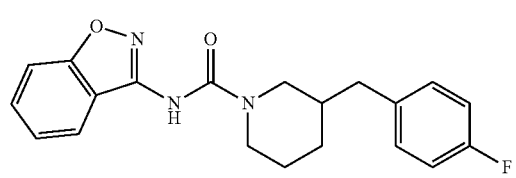 [SMILES: O=C(Nc1noc2ccccc12)N1CCCC(Cc2ccc(F)cc2)C1]

MS (ESI$^+$): calcd for C$_{20}$H$_{20}$FN$_3$O$_2$ m/z 353.15, found 354.2 (M+H)$^+$. $^1$H NMR (CDCl$_3$): 8.50 (s, 1H), 8.06 (d, J=8.0, 1H), 7.55-7.52 (m, 1H), 7.45 (d, J=8.5, 1H), 7.29-7.28 (m, 1H), 7.14-7.12 (m, 2H), 7.00-6.96 (m, 2H), 4.17-4.10 (m, 2H), 3.10-3.04 (m, 1H), 2.79-2.76 (m, 1H), 2.70 (dd, J=6.5, 13.5, 1H), 1.94-1.75 (m, 3H), 1.68-1.52 (m, 1H), 1.28-1.15 (m, 1H).

Example 8

N-Isoxazol-3-yl-3-{[4-(trifluoromethyl)phenyl]methyl}piperidine-1-carboxamide

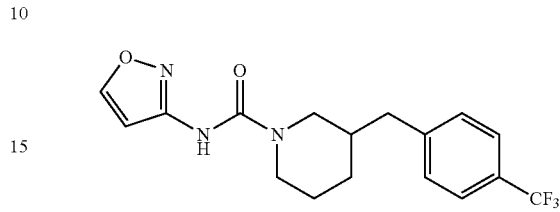

$^1$H NMR (CDCl$_3$): 8.93 (s, 1H), 8.21 (d, J=2.0, 1H), 7.55 (d, J=8.0, 2H), 7.28 (d, J=8.0, 2H), 7.05 (d, J=2.0, 1H), 4.12 (d, J=12.0, 1H), 4.03 (d, J=13.0, 1H), 3.04-2.99 (m, 1H), 2.77-2.72 (m, 2H), 2.54 (dd, J=8.5, 13.5, 1H), 1.94 (br s, 1H), 1.86-1.73 (m, 2H), 1.59-1.45 (m, 1H), 1.29-1.15 (m, 1H).

Example 9

N-Isoxazol-3-yl-3-{[3-(trifluoromethyl)phenyl]methyl}piperidine-1-carboxamide

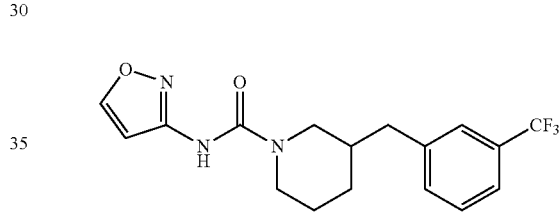

MS (ESI$^+$): calcd for C$_{17}$H$_{18}$F$_3$N$_3$O$_3$ m/z 353.14, found 354.2 (M+H)$^+$. $^1$H NMR (CDCl$_3$): 9.01 (s, 1H), 8.20 (d, J=2.0, 1H), 7.48 (d, J=7.5, 1H), 7.44-7.39 (m, 2H), 7.34 (d, J=7.5, 1H), 7.03 (d, J=2.0, 1H), 4.14 (d, J=13.0, 1H), 4.05 (d, J=13.0, 1H), 3.04-2.99 (m, 1H), 2.78-2.70 (m, 2H), 2.55-2.50 (m, 1H), 1.90-1.86 (m, 1H), 1.82-1.75 (m, 2H), 1.61-1.43 (m, 1H), 1.28-1.16 (m, 1H).

Example 10

3-[3-(4-Fluorophenoxy)benzyl]-N-pyridin-3-ylpiperidine-1-carboxamide

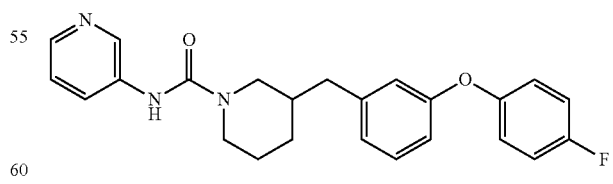

Step A: 3-(4-Fluoro-phenoxy)-bromobenzene. To a solution of 1-bromo-3-iodo-benzene (1.00 g, 3.55 mmol), 4-fluorophenol (462 mg, 3.59 mmol), N,N-dimethylglycine hydrochloride (149 mg, 1.06 mmol), and cesium carbonate (2.28 g, 7.00 mmol) in DMA was added CuI (66.8 mg, 0.351 mmol). The reaction mixture was heated at 90° C. for 48 h, cooled to rt, and then poured into water and extracted with EtOAc (3×). The organic layers were combined, dried (Na$_2$SO$_4$), and concentrated. The crude residue was purified (FCC) to give the title compound as a colorless oil (319 mg, 32%).

Step B: 3-[3-(4-Fluoro-phenoxy)-benzyl]-piperidine-1-carboxylic acid tert-butyl ester. The title compound was prepared using methods analogous to those described in Example 1, Step A.

Step C: 3-[3-(4-Fluoro-phenoxy)-benzyl]-piperidine hydrochloride. The title compound was prepared using methods analogous to those described in Example 1, Step B.

Step D: 3-[3-(4-Fluorophenoxy)benzyl]-N-pyridin-3-ylpiperidine-1-carboxamide. The title compound was prepared using methods analogous to those described in Example 1, Step C. MS (ESI$^+$): calcd for C$_{24}$H$_{24}$FN$_3$O$_2$ m/z 405.18, found 406.2 (M+H)$^+$. $^1$H NMR (d$_4$-methanol): 8.54-8.53 (m, 1H), 8.15 (dd, J=4.8, 1.4, 1H), 7.87 (ddd, J=8.4, 2.6, 1.4, 1H), 7.34-7.31 (m, 1H), 7.25 (t, J=7.9, 1H), 7.08-7.03 (m, 2H), 7.00-6.94 (m, 3H), 6.83-6.81 (m, 1H), 6.79-6.77 (m, 1H), 4.05-4.01 (m, 1H), 4.00-3.95 (m, 1H), 3.03-2.95 (m, 1H), 2.69 (dd, J=13.2, 10.1, 1H), 2.64-2.60 (m, 1H), 2.53-2.48 (m, 1H), 1.85-1.71 (m, 3H), 1.55-1.46 (m, 1H), 1.29-1.21 (m, 1H).

The compounds in Examples 11 to 15 were prepared using methods analogous to those described in Example 10.

Example 11

3-[3-(4-Fluoro-phenoxy)-benzyl]-piperidine-1-carboxylic acid (4-chloro-pyridin-3-yl)-amide

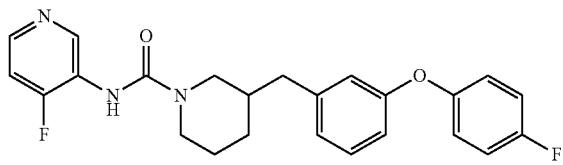 [SMILES: O=C(Nc1cnccc1F)N1CCCC(Cc2cccc(Oc3ccc(F)cc3)c2)C1]

MS (ESI$^+$): calcd for C$_{24}$H$_{23}$ClFN$_3$O$_2$ m/z 439.14, found 440.2 (M+H)$^+$. $^1$H NMR (d$_6$-DMSO): 8.58 (s, 1H), 8.34 (s, 1H), 8.28 (d, J=5.3, 1H), 7.56 (d, J=5.3, 1H), 7.29 (t, J=7.8, 1H), 7.22-7.14 (m, 2H), 7.07-7.01 (m, 2H), 6.97 (d, J=7.6, 1H), 6.86-6.82 (m, 1H), 6.82-6.76 (m, 1H), 3.93 (d, J=13.2, 2H), 2.95-2.87 (m, 1H), 2.68-2.43 (m, 3H), 1.78-1.59 (m, 3H), 1.47-1.29 (m, 1H), 1.23-1.07 (m, 1H).

Example 12

3-[3-(4-Fluoro-phenoxy)-benzyl]-piperidine-1-carboxylic acid imidazo[1,2-b]pyridazin-3-ylamide

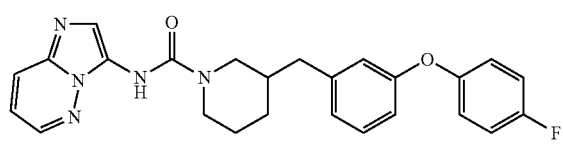 [SMILES: O=C(Nc1cnc2cccnn12)N1CCCC(Cc2cccc(Oc3ccc(F)cc3)c2)C1]

MS (ESI$^+$): calcd for C$_{25}$H$_{24}$FN$_5$O$_2$ m/z 445.19, found 446.2 (M+H)$^+$. $^1$H NMR (d$_6$-DMSO): 8.80 (s, 1H), 8.64-8.61 (m, 1H), 8.16 (dd, J=9.2, 1.4, 1H), 7.78 (s, 1H), 7.34 (dd, J=9.2, 4.5, 1H), 7.29 (t, J=7.8, 1H), 7.21-7.14 (m, 2H), 7.07-7.01 (m, 2H), 6.98 (d, J=7.6, 1H), 6.87-6.83 (m, 1H), 6.82-6.77 (m, 1H), 3.97 (d, J=12.9, 2H), 2.91 (s, 1H), 2.70-2.44 (m, 3H), 1.81-1.59 (m, 3H), 1.41 (m, 1H), 1.24-1.12 (m, 1H).

Examples 13 and 14 were resolved using chiral column chromatography: Jasco Preparative SFC System using a Phenomenex Lux II column (5 μm 250×21 mm, L×I.D.) @ 40° C., 150 bar, 8.3 mL/min ethanol with 0.2% triethylamine and 33.3 mL/min CO$_2$, detection at 220 nm. Retention times: Example 13, (+)-enantiomer: 33-38 minutes; Example 14, (−)-enantiomer: 42-48 minutes.

Example 13

(+)-3-[3-(4-Chloro-phenoxy)-benzyl]-piperidine-1-carboxylic acid pyridin-3-ylamide

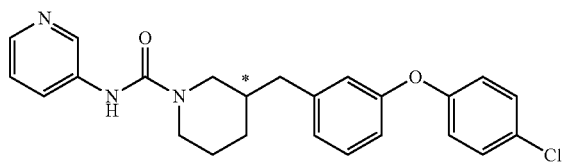 [SMILES: O=C(Nc1cccnc1)N1CCCC(Cc2cccc(Oc3ccc(Cl)cc3)c2)C1]

MS (ESI$^+$): calcd for C$_{24}$H$_{24}$ClN$_3$O$_2$ m/z 421.16, found 422.2 (M+H)$^+$. $^1$H NMR (d$_6$-DMSO): 8.64-8.58 (m, 2H), 8.13 (dd, J=4.6, 1.5, 1H), 7.86-7.81 (m, 1H), 7.40 (d, J=9.0, 2H), 7.32 (t, J=7.8, 1H), 7.24 (dd, J=8.3, 4.7, 1H), 7.05-6.98 (m, 3H), 6.91-6.88 (m, 1H), 6.88-6.84 (m, 1H), 4.01-3.92 (m, 2H), 2.90-2.82 (m, 1H), 2.63-2.43 (m, 3H), 1.75-1.61 (m, 3H), 1.45-1.31 (m, 1H), 1.22-1.07 (m, 1H); [α]$^{23}_D$+22.4 (c 0.15, MeOH).

Example 14

(−)-3-[3-(4-Chloro-phenoxy)-benzyl]-piperidine-1-carboxylic acid pyridin-3-ylamide

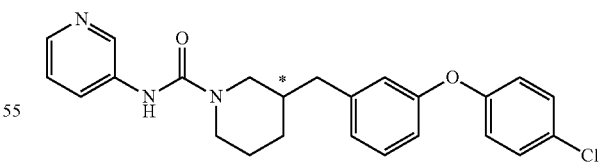

MS (ESI$^+$): calcd for C$_{24}$H$_{24}$ClN$_3$O$_2$ m/z 421.16, found 422.2 (M+H)$^+$. $^1$H NMR (d$_6$-DMSO): 8.64-8.58 (m, 2H), 8.13 (dd, J=4.6, 1.5, 1H), 7.86-7.81 (m, 1H), 7.40 (d, J=9.0, 2H), 7.32 (t, J=7.8, 1H), 7.24 (dd, J=8.3, 4.7, 1H), 7.05-6.98 (m, 3H), 6.91-6.88 (m, 1H), 6.88-6.84 (m, 1H), 4.01-3.92 (m, 2H), 2.90-2.82 (m, 1H), 2.63-2.43 (m, 3H), 1.75-1.61 (m, 3H), 1.45-1.31 (m, 1H), 1.22-1.07 (m, 1H); [α]$^{23}_D$−22.0 (c 0.15, MeOH).

Example 15

3-[3-(4-Trifluoromethoxy-phenoxy)-benzyl]-piperidine-1-carboxylic acid pyridine-3-ylamide

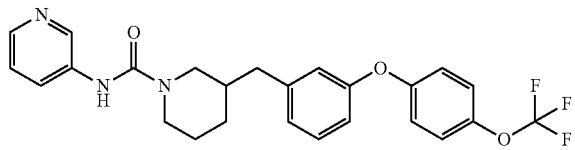 [SMILES: O=C(Nc1cccnc1)N1CCCC(Cc2cccc(Oc3ccc(OC(F)(F)F)cc3)c2)C1]

MS (ESI$^+$): calcd for $C_{25}H_{24}F_3N_3O_3$ m/z 471.18, found 472.2 (M+H)$^+$. $^1$H NMR (d$_6$-DMSO): 8.35 (br s, 1H), 8.27 (br s, 1H), 7.99-7.95 (m, 1H), 7.31-7.27 (m, 1H), 7.24-7.20 (m, 1H), 7.19-7.15 (m, 2H), 6.99 (d, J=9.1, 2H), 6.95 (d, J=7.5, 1H), 6.88-6.84 (m, 2H), 6.26 (s, 1H), 3.94-3.88 (m, 1H), 3.87-3.82 (m, 1H), 3.09-3.01 (m, 1H), 2.69 (dd, J=13.2, 9.8, 1H), 2.62 (dd, J=13.8, 7.2, 1H), 2.54 (dd, J=13.8, 7.0, 1H), 1.92-1.83 (m, 2H), 1.81-1.74 (m, 1H), 1.59-1.50 (m, 1H), 1.29-1.20 (m, 1H).

The compounds in Examples 16 to 19 were prepared using methods analogous to those described in Example 1.

Example 16

3-Quinolin-3-ylmethyl-piperidine-1-carboxylic acid pyridin-3-ylamide

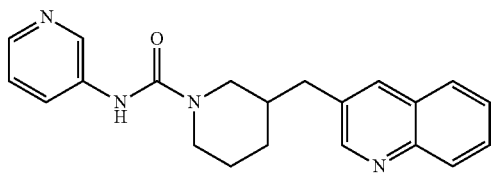 [SMILES: O=C(Nc1cccnc1)N1CCCC(Cc2cnc3ccccc3c2)C1]

MS (ESI$^+$): calcd for $C_{21}H_{22}N_4O$ m/z 346.18, found 347.2 (M+H)$^+$. $^1$H NMR (d$_6$-DMSO): 8.77 (d, J=2.2, 1H), 8.36 (d, J=2.5, 1H), 8.26 (dd, J=4.7, 1.3, 1H), 8.09 (d, J=8.5, 1H), 7.96-7.91 (m, 2H), 7.76 (dd, J=8.2, 1.0, 1H), 7.71-7.66 (m, 1H), 7.56-7.51 (m, 1H), 7.21 (dd, J=8.3, 4.7, 1H), 6.33 (s, 1H), 4.08-4.01 (m, 1H), 3.89-3.81 (m, 1H), 3.11-3.02 (m, 1H), 2.87 (dd, J=13.9, 6.7, 1H), 2.81-2.67 (m, 2H), 2.06-1.95 (m, 1H), 1.92-1.84 (m, 1H), 1.84-1.75 (m, 1H), 1.61-1.49 (m, 1H), 1.35-1.24 (m, 1H).

Example 17

3-(3,4-Dichloro-benzyl)-piperidine-1-carboxylic acid pyridin-3-ylamide

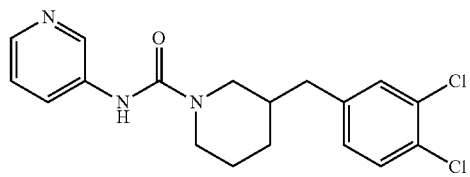 [SMILES: O=C(Nc1cccnc1)N1CCCC(Cc2ccc(Cl)c(Cl)c2)C1]

MS (ESI$^+$): calcd for $C_{18}H_{19}Cl_2N_3O$ m/z 363.09, found 364.1 (M+H)$^+$. $^1$H NMR (d$_6$-DMSO): 8.39 (d, J=2.4, 1H), 8.27 (dd, J=4.7, 1.4, 1H), 7.95 (ddd, J=8.4, 2.6, 1.5, 1H), 7.36 (d, J=8.2, 1H), 7.27 (s, 1H), 7.22 (dd, J=8.3, 4.7, 1H), 7.01 (dd, J=8.2, 2.0, 1H), 6.28 (s, 1H), 4.00-3.93 (m, 1H), 3.87-3.80 (m, 1H), 3.08-3.00 (m, 1H), 2.67 (dd, J=13.2, 10.0, 1H), 2.64-2.57 (m, 1H), 2.48 (dd, J=13.8, 7.4, 1H), 1.90-1.73 (m, 3H), 1.60-1.48 (m, 1H), 1.27-1.16 (m, 1H).

Example 18

3-(3-Trifluoromethoxy-benzyl)-piperidine-1-carboxylic acid pyridin-3-ylamide

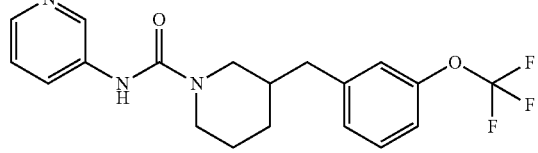

MS (ESI$^+$): calcd for $C_{19}H_{20}F_3N_3O_2$ m/z 379.15, found 380.2 (M+H)$^+$. $^1$H NMR (d$_6$-DMSO): 8.36 (d, J=2.5, 1H), 8.26 (dd, J=4.7, 1.3, 1H), 7.95 (ddd, J=8.3, 2.5, 1.4, 1H), 7.32 (t, J=7.9, 1H), 7.22 (dd, J=8.3, 4.7, 1H), 7.12-7.07 (m, 2H), 7.02 (s, 1H), 6.34 (s, 1H), 3.98-3.92 (m, 1H), 3.91-3.84 (m, 1H), 3.06-2.98 (m, 1H), 2.72-2.64 (m, 2H), 2.54 (dd, J=13.7, 7.5, 1H), 1.92-1.81 (m, 2H), 1.80-1.74 (m, 1H), 1.59-1.49 (m, 1H), 1.28-1.18 (m, 1H).

Example 19

3-(4-Trifluoromethoxy-benzyl)-piperidine-1-carboxylic acid pyridin-3-ylamide

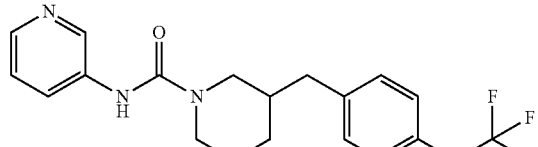

MS (ESI$^+$): calcd for $C_{19}H_{20}F_3N_3O_2$ m/z 379.15, found 380.2 (M+H)$^+$. $^1$H NMR (d$_6$-DMSO): 8.37 (d, J=2.4, 1H), 8.26 (dd, J=4.7, 1.4, 1H), 7.94 (ddd, J=8.4, 2.6, 1.5, 1H), 7.24-7.12 (m, 5H), 6.32 (s, 1H), 3.98-3.91 (m, 1H), 3.89-3.81 (m, 1H), 3.08-2.99 (m, 1H), 2.73-2.62 (m, 2H), 2.52 (dd, J=13.8, 7.3, 1H), 1.91-1.73 (m, 3H), 1.60-1.48 (m, 1H), 1.29-1.16 (m, 1H).

The compounds in Examples 20 to 23 can be synthesized using the synthetic schemes given in Example 10.

Example 20

3-[3-(4-Fluoro-phenoxy)-benzyl]-piperidine-1-carboxylic acid (1H-pyrrolo[2,3-b]pyridin-4-yl)-amide

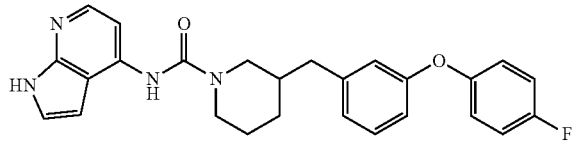 [SMILES: O=C(Nc1ccnc2[nH]ccc12)N1CCCC(Cc2cccc(Oc3ccc(F)cc3)c2)C1]

Example 21

3-[3-(4-Fluoro-phenoxy)-benzyl]-piperidine-1-carboxylic acid isoxazolo[4,5-c]pyridin-3-ylamide

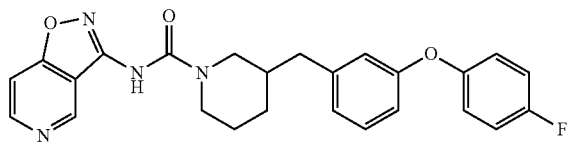 [SMILES: O=C(Nc1noc2ccncc12)N1CCCC(Cc2cccc(Oc3ccc(F)cc3)c2)C1]

Example 22

3-[3-(4-Fluoro-phenoxy)-benzyl]-piperidine-1-carboxylic acid isoxazolo[5,4-c]pyridin-3-ylamide

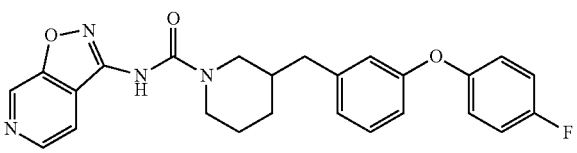 [SMILES: O=C(Nc1noc2cnccc12)N1CCCC(Cc2cccc(Oc3ccc(F)cc3)c2)C1]

Example 23

3-[3-(4-Fluoro-phenoxy)-benzyl]-piperidine-1-carboxylic acid imidazo[1,2-a]pyridin-8-ylamide

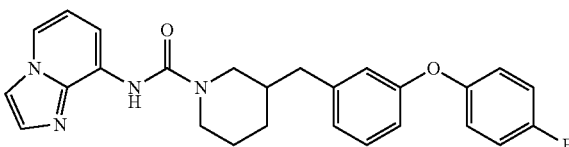

Example 24

3-[3-(4-Fluoro-phenoxy)-benzyl]-piperidine-1-carboxylic acid imidazo[1,2-a]pyridin-7-ylamide

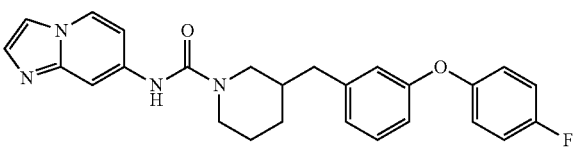 [SMILES: O=C(Nc1ccn2ccnc2c1)N1CCCC(Cc2cccc(Oc3ccc(F)cc3)c2)C1]

To a solution consisting of 1 equivalent of imidazo[1,2-a]pyridin-7-ylamine in CH$_2$Cl$_2$ is added 1 equivalent of N,N'-disuccinimidyl carbonate and 1 equivalent of 4-dimethylaminopyridine (DMAP). The reaction mixture is stirred at rt for 6 h, then treated with 1 equivalent of 3-[3-(4-fluoro-phenoxy)-benzyl]-piperidine hydrochloride and 2 equivalents of diisopropylethylamine and stirred for an additional 16 h at rt. The reaction mixture is diluted with EtOAc and extracted with H$_2$O then saturated aqueous NaCl. The organic layer is dried (MgSO$_4$) and concentrated. The crude residue is purified (FCC, 2 N NH$_3$ in MeOH/DCM) to give 3-[3-(4-Fluoro-phenoxy)-benzyl]-piperidine-1-carboxylic acid imidazo[1,2-a]pyridin-7-ylamide.

The compounds in Examples 25 to 28 can be synthesized using the synthetic scheme given in Example 24.

Example 25

3-[3-(4-Fluoro-phenoxy)-benzyl]-piperidine-1-carboxylic acid imidazo[1,2-a]pyridin-5-ylamide

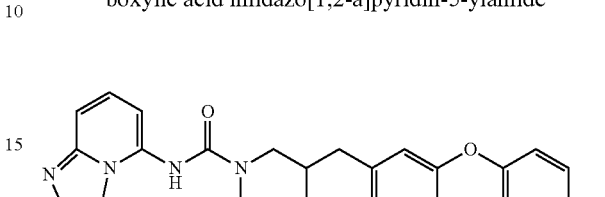

Example 26

3-[3-(4-Fluoro-phenoxy)-benzyl]-piperidine-1-carboxylic acid imidazo[1,2-a]pyrimidin-7-ylamide

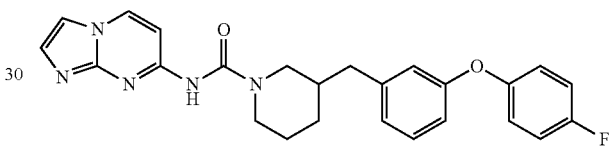

Example 27

3-[3-(4-Fluoro-phenoxy)-benzyl]-piperidine-1-carboxylic acid imidazo[1,2-a]pyrimidin-5-ylamide

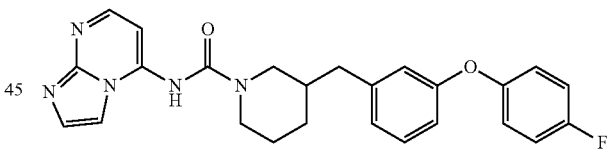

Example 28

3-[3-(4-Fluoro-phenoxy)-benzyl]-piperidine-1-carboxylic acid imidazo[1,2-c]pyrimidin-7-ylamide

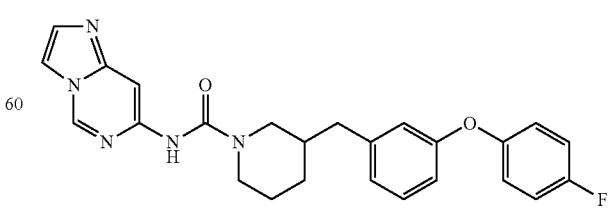

The compounds in Examples 29 to 32 can be synthesized using the synthetic schemes given in Example 10.

Example 29

3-[3-(4-Fluoro-phenoxy)-benzyl]-piperidine-1-carboxylic acid (4-cyano-pyridin-3-yl)-amide

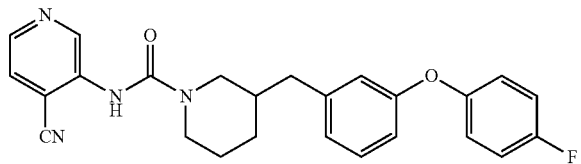 [SMILES: N#Cc1ccncc1NC(=O)N1CCCC(Cc2cccc(Oc3ccc(F)cc3)c2)C1]

Example 30

3-[3-(4-Fluoro-phenoxy)-benzyl]-piperidine-1-carboxylic acid quinolin-8-ylamide

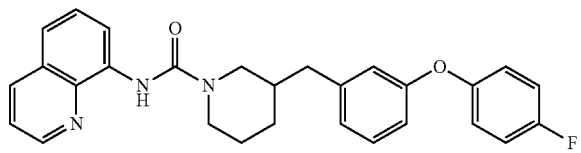 [SMILES: O=C(Nc1cccc2cccnc12)N1CCCC(Cc2cccc(Oc3ccc(F)cc3)c2)C1]

Example 31

3-[3-(4-Fluoro-phenoxy)-benzyl]-piperidine-1-carboxylic acid isoquinolin-5-ylamide

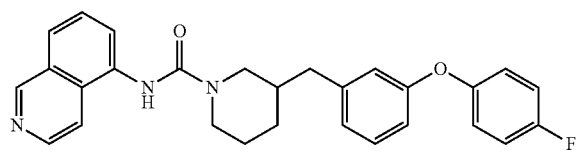 [SMILES: O=C(Nc1cccc2cnccc12)N1CCCC(Cc2cccc(Oc3ccc(F)cc3)c2)C1]

Example 32

3-[3-(4-Trifluoromethyl-phenoxy)-benzyl]-piperidine-1-carboxylic acid pyridin-3-ylamide

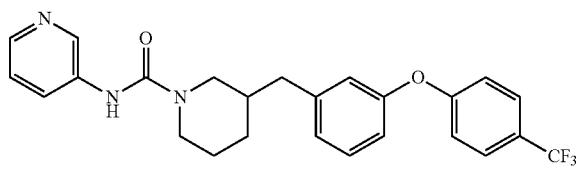 [SMILES: O=C(Nc1cccnc1)N1CCCC(Cc2cccc(Oc3ccc(C(F)(F)F)cc3)c2)C1]

The compound in Example 33 can be synthesized using the synthetic schemes given in Example 1.

Example 33

3-(4-Chloro-3-trifluoromethoxy-benzyl)-piperidine-1-carboxylic acid pyridin-3-ylamide

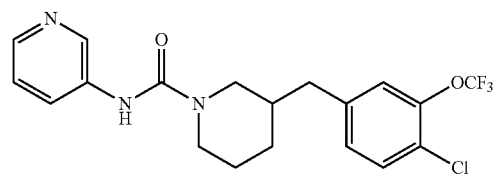 [SMILES: O=C(Nc1cccnc1)N1CCCC(Cc2ccc(Cl)c(OC(F)(F)F)c2)C1]

Biological Testing:
Assay Method 1
A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled human FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Assay Method 2
A. Transfection of Cells with Rat FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent.

These cells were removed from the dish with trypsin and pelleted in a clinical centrifuge. The pellet was re-suspended in 400 μL complete media and transferred to an electroporation cuvette with a 0.4 cm gap between the electrodes. Supercoiled rat FAAH cDNA (1 μg) was added to the cells and mixed. The voltage for the electroporation was set at 0.25 kV, and the capacitance was set at 960 After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Results for compounds tested in these assays are summarized in Table 1, as an average of results obtained. Compounds were tested in free base, hydrochloride salt, and/or trifluoroacetic acid salt forms. Where activity is shown as greater than (>) a particular value, the value is the solubility limit of the compound in the assay medium or the highest concentration tested in the assay.

TABLE 1

| Ex. | Assay 1 IC$_{50}$ (μM) | Assay 2 IC$_{50}$ (μM) |
| --- | --- | --- |
| 1 | 0.410 | 0.604 |
| 2 | 8.000 | >10 |
| 3 | 8.000 | 10.000 |
| 4 | 10.000 | >10 |
| 5 | 2.000 | 0.183 |
| 6 | 0.645 | 0.050 |
| 7 | 2.000 | 0.152 |
| 8 | 10.000 | >10 |
| 9 | 7.000 | 8.999 |

TABLE 1-continued

| Ex. | Assay 1 IC$_{50}$ (μM) | Assay 2 IC$_{50}$ (μM) |
| --- | --- | --- |
| 10 | 0.018 | 0.019 |
| 11 | 0.087 | 0.008 |
| 12 | 0.056 | 0.007 |
| 13 | 0.019 | 0.031 |
| 14 | 0.073 | 0.027 |
| 15 | 0.011 | 0.017 |
| 16 | 1.000 | >10 |
| 17 | 0.048 | 0.180 |
| 18 | 0.190 | 0.450 |
| 19 | 0.430 | 1.600 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A chemical entity selected from compounds of Formula (I):

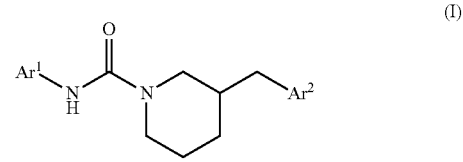

wherein:

Ar$^1$ is pyridyl, independently unsubstituted or substituted with halo, —C$_{1-4}$alkyl, —OC$_{1-4}$alkyl, —OCF$_3$, —CN, or —CF$_3$;

Ar$^2$ is (i) phenyl unsubstituted or substituted with one or two R$^a$ moieties;
where each R$^a$ moiety is independently —C$_{1-8}$alkyl, —OC$_{1-8}$alkyl, halo, —CF$_3$, —OCF$_3$, —OCH$_2$CF$_3$, —S(O)$_{0-2}$C$_{1-8}$alkyl, —S(O)$_{0-2}$CF$_3$, —CO$_2$H, —N(R$^b$)R$^c$, —SO$_2$NR$^b$R$^c$, —NR$^b$SO$_2$R$^c$, —C(O)NR$^b$R$^c$, or —NO$_2$;
or two adjacent R$^a$ moieties taken together form —O(CH$_2$)$_{1-2}$O— or —OCF$_2$O—;
where R$^b$ and R$^c$ are each independently —H or —C$_{1-8}$alkyl, or optionally R$^b$ and R$^c$ taken together with the atoms of attachment form a 4-8 membered ring; or (ii) phenyl substituted at the 3- or 4-position with -L-Ar$^3$, unsubstituted or substituted with one or two R$^a$ moieties, wherein:
L is a linker selected from the group consisting of —(CH$_2$)$_{1-6}$—, —CH═CH—, —O—, —C$_{1-6}$alkyl-O—C$_{1-6}$alkyl-, —C$_{1-6}$alkyl-N(C$_{1-6}$alkyl)-C$_{1-6}$alkyl-, —C$_{1-6}$alkyl-S(O)$_{0-2}$C$_{1-6}$alkyl-, —C≡C—, —C(O)—, or a covalent bond;

Ar$^3$ is:

(a) phenyl unsubstituted or substituted with one or two R$^a$ moieties;
(b) a monocyclic heteroaryl group unsubstituted or substituted with one or two R$^a$ moieties; or
(c) a 9- or 10-membered fused bicyclic heteroaryl group unsubstituted or substituted with one or two R$^a$ moieties;

and pharmaceutically acceptable salts of compounds of Formula (I).

2. A chemical entity as in claim 1, wherein $Ar^1$ is pyridyl.

3. A chemical entity as in claim 1, wherein $Ar^1$ is pyridine, optionally substituted with one or two moieties selected from the group consisting of: halo, —$OC_{1-4}$alkyl, —$OCF_3$, and —$CF_3$.

4. A chemical entity as in claim 1, wherein $Ar^2$ is phenyl substituted with one or two $R^a$ moieties.

5. A chemical entity as in claim 4, wherein each $R^a$ moiety is independently selected from the group consisting of: chloro, cyano, isobutyl, methylsulfanyl, methanesulfonyl, trifluoromethyl, trifluoromethoxy, 2,2,2-trifluoroethoxy, fluoro, methyl, methoxy, tert-butyl, bromo, methoxycarbonyl, cyanomethyl, methoxycarbonylmethyl, trifluoromethanesulfonyl, trifluoromethanesulfanyl, and butyl; or two adjacent $R^a$ moieties taken together form —$OCH_2O$— or —$OCF_2O$—.

6. A chemical entity as in claim 4, wherein each $R^a$ moiety is independently selected from the group consisting of: F, Cl, Br, $CF_3$, or two adjacent $R^a$ moieties taken together form —$OCF_2O$—.

7. A chemical entity as in claim 1, wherein $Ar^2$ is phenyl substituted at the 3- or 4-position with -L-$Ar^3$, unsubstituted or substituted with one or two $R^a$ moieties.

8. A chemical entity as in claim 7, wherein L is —$CH_2CH_2$—, —O—, —$OCH_2$—, or —C≡C—.

9. A chemical entity as in claim 7, wherein L is —O—.

10. A chemical entity as in claim 7, wherein $Ar^3$ is phenyl, unsubstituted or substituted with one or two $R^a$ moieties.

11. A chemical entity as in claim 10, wherein each $R^a$ moiety is Independently selected from the group consisting of: chloro, cyano, isobutyl, methylsulfanyl, methanesulfonyl, trifluoromethyl, trifluoromethoxy, 2,2,2-trifluoroethoxy, fluoro, methyl, methoxy, tert-butyl, bromo, methoxycarbonyl, cyanomethyl, methoxycarbonylmethyl, trifluoromethanesulfonyl, trifluoromethanesulfanyl, and butyl; or two adjacent $R^a$ moieties taken together form —$OCH_2O$— or —$OCF_2O$—.

12. A chemical entity as in claim 10, wherein each $R^a$ moiety is independently fluoro.

13. A chemical entity selected from the group consisting of:
3-(2,2-difluoro-benzo[1,3]dioxol-5-ylmethyl)-piperidine-1-carboxylic acid pyridin-3-ylamide;
3-[3-(4-fluorophenoxy)benzyl]-N-pyridin-3-ylpiperidine-1-carboxamide;
3-[3-(4-fluoro-phenoxy)-benzyl]-piperidine-1-carboxylic acid (4-chloro-pyridin-3-yl)-amide;
(+)-3-[3-(4-chloro-phenoxy)-benzyl]-piperidine-1-carboxylic acid pyridin-3-ylamide;
(−)-3-[3-(4-chloro-phenoxy)-benzyl]-piperidine-1-carboxylic acid pyridin-3-ylamide;
3-[3-(4-trifluoromethoxy-phenoxy)-benzyl]-piperidine-1-carboxylic acid pyridine-3-ylamide;
3-(3,4-dichloro-benzyl)-piperidine-1-carboxylic acid pyridin-3-ylamide;
3-(3-trifluoromethoxy-benzyl)piperidine-1-carboxylic acid pyridin-3-ylamide;
3-(4-trifluoromethoxy-benzyl)piperidine-1-carboxylic acid pyridin-3-ylamide;
3-[3-(4-fluoro-phenoxy)-benzyl]-piperidine-1-carboxylic acid (4-cyano-pyridin-3-yl)-amide;
3-[3-(4-trifluoromethyl-phenoxy)-benzyl]-piperidine-1-carboxylic acid pyridin-3-ylamide;
3-(4-chloro-3-trifluoromethoxy-benzyl)piperidine-1-carboxylic acid pyridin-3-ylamide;
and pharmaceutically acceptable salts thereof.

14. A pharmaceutical composition comprising:
(a) an effective amount of at least one chemical entity selected from compounds of Formula (I):

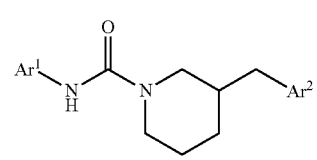

wherein:
$Ar^1$ is pyridyl, independently unsubstituted or substituted with halo, —$C_{1-4}$alkyl, —$OC_{1-4}$alkyl, —$OCF_3$, —CN, or —$CF_3$;
$Ar^2$ is
  (i) phenyl unsubstituted or substituted with one or two $R^a$ moieties;
    where each $R^a$ moiety is independently —$C_{1-8}$alkyl, —$OC_{1-8}$alkyl, halo, —$CF_3$, —$OCF_3$, —$OCH_2CF_3$, —$S(O)_{0-2}C_{1-8}$alkyl, —$S(O)_{0-2}CF_3$, —$CO_2H$, —$N(R^b)R^c$, —$SO_2NR^bR^c$, —$NR^bSO_2R^c$, —$C(O)NR^bR^c$, or —$NO_2$;
    or two adjacent $R^a$ moieties taken together form —$O(CH_2)_{1-2}O$— or —$OCF_2O$—;
    where $R^b$ and $R^c$ are each independently —H or —$C_{1-8}$alkyl, or optionally $R^b$ and $R^c$ taken together with the atoms of attachment form a 4-8 membered ring; or
  (ii) phenyl substituted at the 3- or 4-position with -L-$Ar^3$, unsubstituted or substituted with one or two $R^a$ moieties, wherein:
    L is a linker selected from the group consisting of —$(CH_2)_{1-6}$—, —CH=CH—, —O—, —$C_{1-6}$alkyl-O—$C_{1-6}$alkyl-, —$C_{1-6}$alkyl-N($C_{1-6}$alkyl)-$C_{1-6}$alkyl-, —$C_{1-6}$alkyl-S(O)$_{0-2}C_{1-6}$alkyl-, —C≡C—, —C(O)—, or a covalent bond;
    $Ar^3$ is:
      (a) phenyl unsubstituted or substituted with one or two $R^a$ moieties;
      (b) a monocyclic heteroaryl group unsubstituted or substituted with one or two $R^a$ moieties; or
      (c) a 9- or 10-membered fused bicyclic heteroaryl group unsubstituted or substituted with one or two $R^a$ moieties;
and pharmaceutically acceptable salts of compounds of Formula (I); and
(b) a pharmaceutically acceptable excipient.

15. A pharmaceutical composition according to claim 14, wherein said at least one chemical entity is selected from the group consisting of:
3-(2,2-difluoro-benzo[1,3]dioxol-5-ylmethyl)-piperidine-1-carboxylic acid pyridin-3-ylamide;
3-[3-(4-fluorophenoxy)benzyl]-N-pyridin-3-ylpiperidine-1-carboxamide;
3-[3-(4-fluoro-phenoxy)-benzyl]-piperidine-1-carboxylic acid (4-chloro-pyridin-3-yl)-amide;
(+)-3-[3-(4-chloro-phenoxy)-benzyl]-piperidine-1-carboxylic acid pyridin-3-ylamide;
(−)-3-[3-(4-chloro-phenoxy)-benzyl]-piperidine-1-carboxylic acid pyridin-3-ylamide;
3-[3-(4-trifluoromethoxy-phenoxy)-benzyl]-piperidine-1-carboxylic acid pyridine-3-ylamide;
3-(3,4-dichloro-benzyl)-piperidine-1-carboxylic acid pyridin-3-ylamide;

3-(3-trifluoromethoxy-benzyl)piperidine-1-carboxylic acid pyridin-3-ylamide;

3-(4-trifluoromethoxy-benzyl)piperidine-1-carboxylic acid pyridin-3-ylamide;

3-[3-(4-fluoro-phenoxy)-benzyl]-piperidine-1-carboxylic acid (4-cyano-pyridin-3-yl)-amide;

3-[3-(4-trifluoromethyl-phenoxy)-benzyl]-piperidine-1-carboxylic acid pyridin-3-ylamide;

3-(4-chloro-3-trifluoromethoxy-benzyl)piperidine-1-carboxylic acid pyridin-3-ylamide;

and pharmaceutically acceptable salts thereof.

16. A pharmaceutical composition according to claim 14, further comprising: an analgesic selected from the group consisting of opioids and non-steroidal anti-inflammatory drugs.

17. A pharmaceutical composition according to claim 14, further comprising: an additional active ingredient selected from the group consisting of aspirin, acetaminophen, opioids, ibuprofen, naproxen, COX-2 inhibitors, gabapentin, pregabalin, and tramadol.

* * * * *